United States Patent [19]

Aswad

[11] Patent Number: 5,273,886
[45] Date of Patent: Dec. 28, 1993

[54] DETERMINATION OF ISOASPARTATE IN PROTEINS

[75] Inventor: Dana W. Aswad, Irvine, Calif.

[73] Assignee: The Regents of the University of California, Oakland, Calif.

[21] Appl. No.: 573,336

[22] Filed: Aug. 24, 1990

[51] Int. Cl.$^5$ ............................................. C12Q 1/48
[52] U.S. Cl. ................................. 435/15; 435/23; 435/68.1; 435/193; 436/161; 436/86; 514/45; 514/46; 530/300; 530/335; 530/344; 530/345; 930/20; 930/22
[58] Field of Search .................. 435/23, 15, 68.1, 193; 436/161, 86; 514/46, 45; 530/300, 335, 344, 345; 930/20, 22

[56] References Cited

PUBLICATIONS

Aswad, et al., "The Unusual Substrate Specificity of Eukaryotic Protein Carboxyl Methyltransferases" *Trends in Biochem. Sciences,* vol. 12, No. 4, 155 (1987).

Aswad, et al., "Modification of Synthetic Peptides Related to Lactate Dehydrogenase (231-242) by Protein Carboxyl Methyltransferase and Tyrosine Protein Kinase: Effects of Introducing an Isopeptide Bond between Aspartic Acid-235 and serine 236", *Biochemistry* 26, 675 (1987).

Aswad, et al., "Stoichiometric Methylation of Porcine Adrenocorticotropin by Protein Carboxyl Methyltransferase Requires Deamidation of Asparagine 25", *J. of Biol. Chem.* 17, (1984).

Aswad, et al., "Formation of Isoaspartate in Calmodulin and Human Growth Hormone", *J. Cell Biochem. Supplement 13A,* UCLA Symposia on Molecular & Cellular Biology, 18, 65 A202 (1989).

Graf et al., "Revised Amide Location for Porcine and Human Andrenocorticotropic Hormone", *Acta Biochim. et Biophys. Acad. Sci. Hung.,* vol. 6 (4), 415-418 (1971).

Di Donato, et al., "Selective Deamidation and Enzymatic Methylation of seminal Ribonuclease", *Biochemistry* 25, 8361-8368 (1986).

Galletti, et al., "Mechanism of Protein Carboxyl Methyl Transfer Reactions: Structural Requirements of Methyl Accepting Substrates" *Adv. Exper. Med. Biol.* 231 229-245 (1988).

Geiger and Clarke, "Deamidation Isomerization, and Racemization at Asparaginyl and Aspartyl Residues in Peptides", *J. Biol. Chem.* 262 2, 785-794 (1987).

Haley and Corcoran, "β-Aspartyl peptide Formation from an Amino Acid Sequence in Ribonuclease", *Biochemistry* 6, 9 2668-2672 (1967).

Henzel, et al., "The Primary Structure of a Protein Carboxyl Methyltransferase from Bovine Brain that Selectively Methylates L-Isoaspartyl Sites", *J. Biol. Chem.* 264, 27 15905, 15911 (1989).

Ingrosso, et al., "Sequence of the D-Aspartyl/L-Isoaspartyl Protein methyltransferase from Human Erythrocytes", *J. Biol. Chem.* 264, 33 20131-20139 (1989).

Johnson, et al., "Deamidation of Calmodulin at Neutral and Alkaline pH: Quantitative Relationships between Ammonia Loss and the Susceptibility of Calmodulin to Modification by Protein Carboxyl Methyltransferase", *Archives of Biochem. and Biophy.* 268, 1 276-286 (1989).

Johnson, et al., "Protein Carboxyl Methyltransferase Facilitates Conversion of Atypical L-Isoaspartyl Peptides to Normal L-Aspartly Peptides", *J. Biol. Chem.* 262, 12 5622-5629 (1987).

(List continued on next page.)

*Primary Examiner*—Ronald W. Griffin
*Assistant Examiner*—Pamela S. Webber
*Attorney, Agent, or Firm*—Knobbe, Martens, Olson & Bear

[57] ABSTRACT

The invention relates to methods and means for quantitative determination of the isoaspartyl content of polypeptides via selective methylation of their fragments, catalyzed by a protein L-isoaspartyl methyltransferase enzyme. Since deamidation of asparagine side chains at specific sites of proteins and the resultant isoaspartate formation are emerging as a major contributor to protein degradation under mild conditions, the invention also concerns a method for quantitation of protein degradation associated with isoaspartate formation.

62 Claims, 13 Drawing Sheets

OTHER PUBLICATIONS

Johnson, et al., "Formation of Isoasparatate at Two Distinct Sites during in Vitro Aging of Human Growth Hormone" *J. Biol. Chem.* 264, 24 14261–14262 (1989).

McFadden and Clarke, "Conversion of Isoaspartyl Peptides to Normal peptides: Impliciations for the Cellular Repair of Damaged Proteins" *Proc. Natl. Acad. Sci. USA* 84, 2595–2599 (1987).

Murray and Clarke, "Synthetic Peptide Substrates for the Erythorocyte Protein Carboxyl Methyltransferase", *J. Biol. Chem.* 259, 17 10722–10732 (1984).

Ota and Clarke, "Methylation at Specific Altered Aspartyl and Asparaginyl Residues in Glucagon by the Erythorocyte Protein Carboxyl Methyltransferase", *J. Biol. Chem.* 262, 18 8522–853.1 (1987).

Ota and Clarke, "Enzymatic Methylation of L–Isoaspartyl Residues Derived from Aspartyl Residues in Affinity-purified Calmodulin", *J. Biol. Chem.* 264, 1 54–60 (1989).

Pisano, et al., "$\beta$-Aspartylglycine in Urine and Enzymic Hydrolyzates of Proteins", *Archives of Biochem. and Biophys.* 117, 394–399 (1966).

Sato, et al., "Primary Structure of Rat Brain Protein Carboxyl Methyltransferase Deduced from cDNA Sequence", *Biochem. and Biophys. Research Comm.* 16, 1 342–347 (1989).

Spiess, "COOH-Terminal Analysis of Polypeptides by Chemical and Chromatographic Methods", *Methods of Protein Microcharacterization* (Human Press) 363–377 (1986).

Swallow and Abraham, "Formation of $\epsilon$-(Amonosuccinyl)-lysine from $\epsilon$-Aspartyl-lysine from Bacitracin A, and from the Cell Walls of Lactobacilli", *Biochemistry* 70, 364–373 (1958).

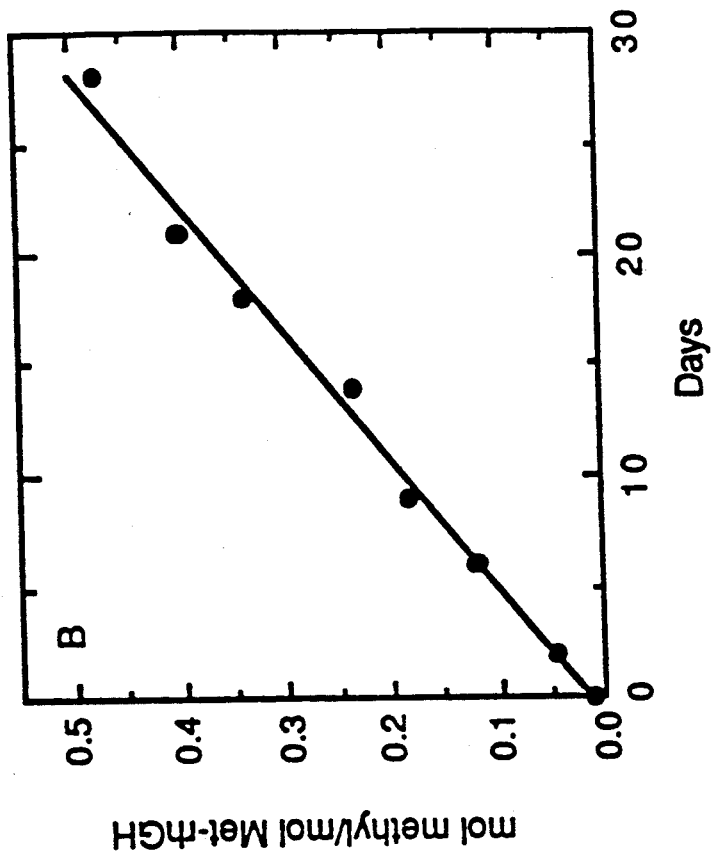
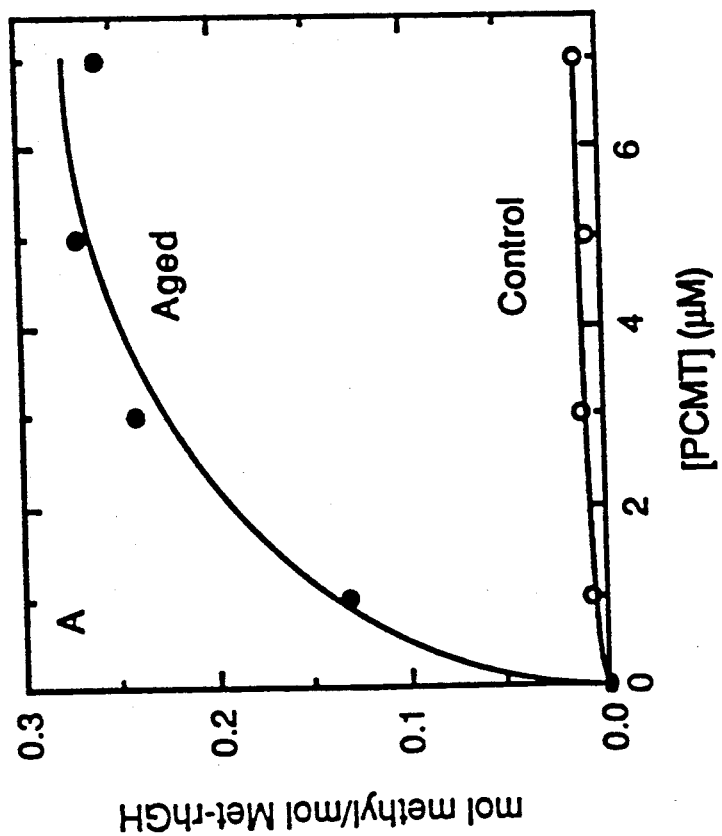
FIG. 2a
FIG. 2b

SEQUENCE OF PROTEIN L-ISOASPARTYL METHYLTRANSFERASE

```
BB1   AWKSGGASHS  ELIHNLRKNG  IIKTDKVFEV  MLATDRSHYA  KCNPYMDSPQ    50
HR1   ----------  ----------  -L--------  ----------  ----------
RB    ----------  ----------  ----------  ----------  -S--------

BB1   SIGFQATISA  PHMHAYALEL  LFDQLNEGAK  ALDVGSGSGI  LTACFARMVG   100
HR1   ----------  ----------  -----H----  ----------  ----------
RB    ----------  ----------  -----H----  -P--------  ----------

BB1   PSGKVIGIDH  IKELVDDSIN  NVRKDDPMLL  SSGRVQLVVG  DGRMGYAAEA   150
HR1   QT--------  ----------  -------T--  ----------  --------E--
RB    H---------  ---------T  --K-------  -----R----  -----F-E--

BB1   PYDAIHVGAA  APVVPQALID  QLKPGGRLIL  PVGPAGGNQM  LEQYDKLQDG   200
HR1   ----------  ----------  ----------  ----------  ----------
RB    ----------  ----------  ----------  ----------  ----------

BB1   SVKMKPLMGV  IYVPLTDKEK  QWSRWK   226
HR1   -I--------  ----------  ------
RB    ----------  ----------  ------
```

BB1: BOVINE BRAIN TYPE I
HENZEL ET AL., J. BIOL. CHEM. 264, 15905-15911 (1989)

RB1: HUMAN RED BLOOD CELL TYPE I
INGROSSO ET AL., J. BIOL. CHEM. 264, 20131-20139 (1989)

RB: RAT BRAIN, FROM cDNA SEQUENCE
SATO ET AL., BIOCHEM. BIOPHYS. RES. COMMUN. 161, 342-347 (1989)

FIG. 11

DETERMINATION OF ISOASPARTATE IN PROTEINS

This invention was made with Government support under Grant Nos. 5-RO1-NS17269, 5-PO1-AG00538, and 5-KO4-NSO1082 awarded by the National Institute of Health. The Government has certain rights on this invention.

FIELD OF THE INVENTION

The invention relates to methods and means for quantitative determination of the isoaspartyl content of polypeptides via selective methylation of their fragments, catalyzed by a protein L-isoaspartyl methyltransferase enzyme. Since deamidation of asparagine side chains at specific sites of proteins and the resultant isoaspartate formation are emerging as a major contributor to protein degradation under mild conditions, the invention also concerns a method for quantitation of protein degradation associated with isoaspartate formation.

BACKGROUND OF THE INVENTION

Although covalent damage to proteins can be caused by numerous reactions involving the side chains of amino acids and the amide linkages of the polypeptide backbone, it has recently been discovered that the deamidation of asparagine side chains at specific sites is a major source of spontaneous structural damage to peptides and proteins in the pH range to which proteins are most typically exposed [Aswad et al., *Adv. Exper. Med. Biol.* 231, 247–259 (1988); Johnson et al., *Arch. Biochem. Biophys.* 268, 276–286 (1989)]. For example, there is evidence that deamidation of asparagine is primarily responsible for the inactivation of lysozyme, triosephosphate isomerase, adrenocorticotropin, and calmodulin. In small peptides, deamidation of asparagine proceeds most rapidly when the amino acid sequence favors intramolecular catalysis, and the formation of a cyclic imide intermediate. Isoaspartyl linkages can also be generated in small peptides through isomerization of aspartate [Swallow and Abraham, *Biochem J.* 70, 364–373 (1958); Geiger and Clarke, *J. Biol. Chem.* 262, 785–794 (1987)]. The mechanisms of the formation of isoaspartyl linkages upon deamidation of asparagine or isomerization of aspartate are illustrated in FIG. 1.

Until now, there has been no direct method for quantitation of the amount of isoaspartate in proteins Essentially three types of methods have been known in the art.

One method is to sequence peptides derived from a protein and look for regions where sequencing fails at a site where aspartate or asparagine would normally be found. This method has been employed to infer the presence of isoaspartate in deaminated adrenocorticotropin [Graf, et al., *Acta Biochem. Biophys. Acad. Sci. Hung.* 6, 415–418 (1971)]. Sequencing a single protein typically requires months to years.

A second method is to digest the protein with a variety of proteases and look specifically for dipeptides containing an isoaspartyl linkage [Haley and Corcoran, *Biochemistry* 6, 2668–2672 (1967); Pisano et al., *Arch. Biochem. Biophys.* 117, 394–399 (1966)]. This method requires several days to analyze one sample, and involves a number of specialized reagents (isoaspartyl dipeptide standards) some of which are not commercially available. This method is also far from being quantitative.

The third method is to incubate the protein in acetic anhydride and pyridine in the presence of extremely high levels of radioactive water ($^3H_2O$), and then subject the protein to amino acid analysis, looking for incorporation of the tritium into aspartate [Spiess, J. in *Methods of Protein Microcharacterization (Humana Press)*, 363–377 (1986)].

Interest in isoaspartate has increased in recent years following the discovery that it is selectively methylated by a protein carboxyl methyltransferase, which is present in a wide variety of species and cell types.

Protein L-isoaspartyl methyl transferases (PIMTs) are enzymes catalyzing methyl ester formation in a broad range of proteins They have an unusual substrate specificity whereby almost any protein, especially if denatured, serves as methyl acceptor to some degree However, the methyl group incorporation is generally substoichiometric, and it appears that only a subpopulation of the molecules in a given protein are capable of functioning as methyl acceptors.

In 1984 the laboratory of Dr. Dana W. Aswad at the University of California, Irvine, and, independently, Dr. Steven Clarke's laboratory at UCLA, discovered that an enzyme then called protein carboxyl methyltransferase (PCMT) or protein methylase II or protein carboxymethylase, exhibited a highly selective methylation of L-isoaspartyl residues in peptides More particularly, it was found that this enzyme catalyzed the methylation of isoaspartate in a damaged (deamidated) form of porcine adrenocorticotropin (ACTH) [Aswad, D.W. *J. Biol. Chem.* 259, 10714–10721 (1984) and Murray, E.D. Jr., and Clarke, S., *J. Biol. Chem.* 259, 10722–10732 (1984)]. Alkaline deamidation of asparagine 25 in ACTH was described to proceed through a cyclic imide intermediate, the hydrolysis of which yielded two products, a peptide which contained a normal α-linked L-aspartyl residue and a peptide with an atypical β-linked L-aspartyl residue. The methyltransferase was found to specifically recognize and methylate the unusual aspartyl residue having a β-carboxyl linkage in position 25 of ACTH.

Subsequent work in these laboratories [Aswad et al., *Biochemistry* 26, 675–682 (1987); Johnson et al., *J. Biol. Chem.* 262, 5622–5629 (1987); Aswad and Johnson, *Trends Biochem. Sci.* 12, 155–158 (1987); Ota, et al., *J. Biol. Chem.* 262, 8522–8531 (1987); Ota and Clarke, *J. Biol. Chem.* 264, 54–60 (1989); McFadden and Clarke, *J. Biol. Chem.* 261, 11503–11511 (1986), and in the laboratory of Dr. Patrizia Galletti in Naples [DiDonato et al., *Biochemistry* 25, 8361–8368 (1986); Galletti et al., *Adv. Exper. Med. Biol.* 231, 229–245 (1988)] indicated that PCMT would methylate isoaspartyl sites in a variety of peptides with little dependence on the surrounding sequence [see e.g. Aswad and Johnson, Supra].

More recently [Henzel et al , *J. Biol. Chem.* 264, 15905–15911 (1989)], this enzyme has been referred to as a protein L-isoaspartyl methyltransferase (PIMT), so as to distinguish it from other protein carboxyl methylating enzymes which do not methylate isoaspartate. Accordingly, hereinafter we shall use this designation.

Existing practice of using PIMT to identify isoaspartate in proteins has been limited to basic scientific applications.

Ota and Clarke, *J. Biol. Chem.* 264, 54–60 (1989) investigated the formation of D-aspartyl and L-isoaspartyl (β-aspartyl) residues and their subsequent methylation in bovine brain calmodulin by PIMT. They subjected intact calmodulin to methylation using partially purified PIMT, and subsequently digested the methylated calmodulin by proteolysis and separated the peptides by HPLC. Because the methylation is performed on the intact-folded protein, any isoaspartates that are buried in the interior of the protein, or held in a rigid conformation, may not be accessible to methylation by PIMT. Moreover, proteolytic digestion of the pre-methylated protein may result in significant loss of the methyl esters We have experimentally found that, for these reasons, this method severely underestimates the amount of isoaspartate in the target protein.

Di Donato et al., *Biochemistry* 25, 8361–8368 (1986) suspected the presence of isoaspartate in a form of ribonuclease (RNAse) They digested the protein with trypsin, then separated the resulting peptides by HPLC. A peptide which was suspected of harboring the isoaspartate was isolated and tested for its ability to accept methyl groups upon incubation with PIMT and radiolabeled S-adenosyl-L-methionine (AdoMet). This approach is suitable for analysis of specific peptides derived from a protein when there is some a priori evidence for location of the isoaspartate. It is not a convenient approach for routine screening of proteins, however, because each peptide would have to be methylated separately. A given protein could result in hundreds of separate methylation reactions for a complete screening Galletti et al., *Adv. Exper. Med. Biol.* 268, 229–245 (1988) have used PIMT to identify isoaspartate in mouse epidermal growth factor. The protein was treated in a manner which was expected to generate isoaspartate. They then unfolded the protein by reducing and chemically blocking the disulfide bonds which normally serve to stabilize the native structure. The unfolded form of EGF showed evidence of significant levels of isoaspartate. Control experiments indicated that the unfolding per se did not generate the isoaspartate, but did allow its detection. A possible problem with this method is that sulfhydryl modification may not always be effective at rendering all possible sites accessible to methylation. Another problem is that the conditions employed for blocking the sulfhydryl groups may inadvertently introduce isoaspartate into the protein leading to artifacts.

In proteins lacking disulfide bonds, this approach is of no use.

Aswad et al., *J. Cell. Biochem. Supplement* 13A, UCLA Symposia on Molecular & Cellular Biology, 18th Annual Meetings, Abstracts, A 202, p. 65 (1989) report the selective methylation of calmodulin and human growth hormone after digestion with trypsin. The peptide fragments were separated by HPLC, and assayed for methyl incorporation.

There is no commercially applicable method known in the art utilizing PIMT for analysis of isoaspartate in proteins.

SUMMARY OF THE INVENTION

The present invention relates to a simple and accurate method for the quantitative determination of the isoaspartyl content of polypeptides based upon methylation catalyzed by PIMT. The invention is based on the novel and unexpected finding that proteins can be digested with a protease and then methylated via the PIMT catalyzed reaction without removing the protease or separating the peptides generated from the analyte protein. The total amount of isoaspartate in the target protein can be quantitatively determined via detection of methyl incorporation into the mixture of peptide fragments The invention also relates to an efficient method for determining the approximate location of isoaspartate within the protein.

Prior art methods utilizing PIMT to identify isoaspartate in proteins have employed methylation of intact (Ota and Clarke, supra) or reduced and alkylated (Galletti et al., supra) protein, or digested the protein into peptide fragments, which were then isolated and separately methylated to identify the isoaspartate-containing species (DiDonato et al., supra). The only reference disclosing reaction conditions for the methylation of a mixture of trypsin digests is Johnson et al., *J. Biol. Chem.* 264-24 (Aug. 25 issue), 14262–14271 (1989).

The present invention provides a much simpler, more rapid, and more sensitive method for determining the amount of isoaspartate in a protein than any existing method. A further advantage is that a substantial portion of the test can be carried out in a single reaction tube.

Also, the utilization of the methylation method according to the present invention in conjunction with peptide separation techniques, will allow the rapid identification of the regions of a protein responsible for the presence of isoaspartate.

In one aspect, the present invention concerns a method for quantitative determination of the isoaspartyl content of a polypeptide comprising quantitatively methylating a mixture comprising fragments of the polypeptide with labeled S-adenosyl-L-methionine, in the presence of a protein L-isoaspartyl methyltransferase (PIMT), and determining the total amount of methyl groups incorporated into the polypeptide fragments without their previous separation, via detection of the signal of the label.

In another aspect, the present invention concerns a method for quantitation of protein degradation associated with isoaspartate formation, comprising the steps of:

(a) providing a mixture comprising fragments of the protein;

(b) quantitatively methylating the mixture with a labeled S-adenosyl-L-methionine in the presence of a protein L-isoaspartyl methyltransferase (PIMT);

(c) quantitatively determining the total amount of the methyl groups incorporated in the polypeptide fragments, without their previous separation, by detecting the signal of the label of S-adenosyl-L-methionine.

In a further aspect, the present invention relates to an assay kit for quantitative determination of isoaspartyl residues in a polypeptide, comprising (a) a protease capable of degrading said polypeptide;

(b) a protease inhibitor capable of terminating proteolysis;

(c) a protein L-isoaspartyl methyltransferase (PIMT);

(d) S-adenosyl-L-methionine; and (e) a pH buffer of about pH 6 to 6.5.

In a still further aspect, the invention concerns a process for selective methylation of L-isoaspartyl residues in a peptide, comprising a) digesting said peptide with a proteolytic enzyme, and b) contacting the digestion mixture comprising fragments of said protein, with S-adenosyl-L-methionine, in the presence of a protein L-isoaspartyl methyltransferase (PIMT).

BRIEF DESCRIPTION OF DRAWINGS

FIG. 2 illustrates in vitro aging of Met-rhGH increases its ability to be methylated by protein carboxyl methyltransferase (PCMT).

FIG. 11 shows the sequences of three different protein L-isoaspartyl methyltransferase.

DETAILED DESCRIPTION OF THE INVENTION

A. Definitions

Figure 1:
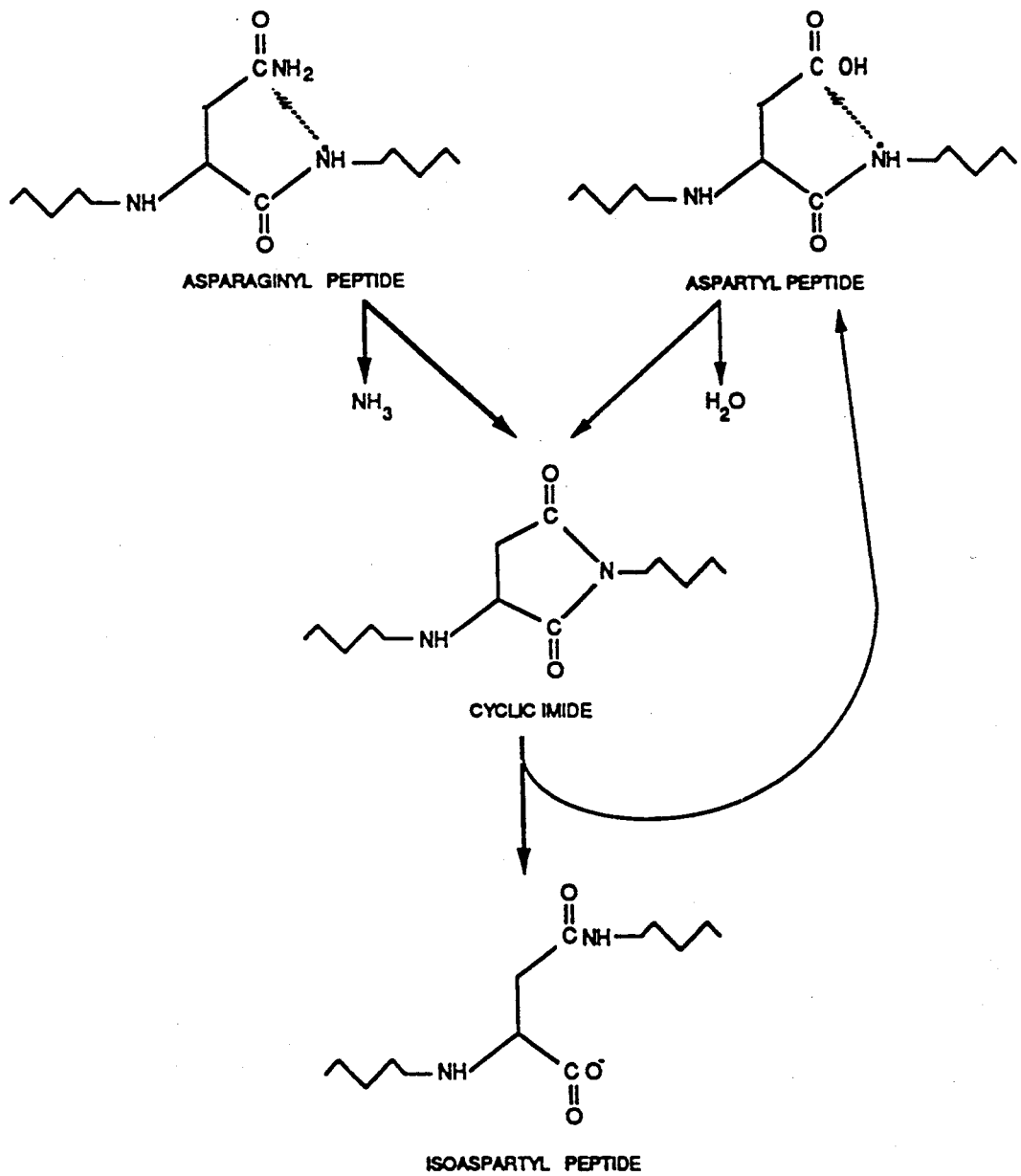
FIG. 1 shows mechanisms for the formation of isoaspartyl linkages upon deamidation of asparagine or isomerization of aspartate.

The present invention concerns a method for determination of the isoaspartyl content of proteins. The terms "isoaspartyl" and "isoaspartate" are used interchangeably, and refer to L-isoaspartyl residues. Isoaspartyl residues are linked to the adjacent amino acid via a peptide bond to their side-chain $\beta$-carboxyl rather than to the main-chain $\alpha$-carboxyl. Accordingly, the $\beta$-carboxyl group of the aspartate is part of the protein backbone, and the $\alpha$-carboxyl group is present as an atypical one-carbon carboxylic acid side chain. Isoaspartyl residues are also referred to as $\beta$-aspartyl, or "$\beta$-linked aspartyl".

The enzyme now called protein isoaspartyl methyltransferase (PIMT) was first identified in 1965 by Axelrod and Daly as a "methanol forming" enzyme, which was thought to catalyze the hydrolysis of S-adenosyl-L-methionine (AdoMet) yielding methanol and S-adenosylhomocysteine. A few years later, an AdoMet-dependent methyl transferase methylating free carboxylic groups in protein substrates was identified. On the basis of their properties and tissue distribution, the two enzymes were found to be identical. As mentioned before, in 1984 it was recognized that this enzyme exhibited a highly selective methylation of L-isoaspartyl residues. Especially in the early literature, this enzyme is referred to as protein carboxyl methyltransferase (PCMT), or protein methylase II or protein carboxymethylase; and the enzymes referred to by these names are all encompassed by the present definition, provided they are capable of selected methylation of L-isoaspartyl residues.

PIMT has been isolated from different sources, and the obtained enzymes may have certain structural differences, including variations in their amino acid sequence. The amino acid sequence of bovine brain type I (RBI) PIMT was first reported by Henzel et al., *J. Biol. Chem.* 264, 15905-15911 (1989). The sequence of human red blood type I (RBI) PIMT was disclosed by Ingrosso et al., *J. Biol. Chem.* 264, 20131-20139 (1989). The amino acid sequence of rat brain (RB) PIMT was first determined by Sato et al., *Biochem. Biophys. Res. Comm.* 61, 342-347 (1989). A comparison of these sequences, showing the differences, is presented in FIG. 11.

The term "PIMT" is given a functional definition, and refers to any enzyme which catalyzes the transfer of the active methyl group of S-adenosyl-L-methionine onto the atypical $\alpha$-carboxyl group of L-isoaspartyl residues.

It is noted that some laboratories have referred to these enzymes as the D-aspartyl/L-isoaspartyl protein carboxyl methyltransferase (e.g. Ota and Clarke, supra), however, none has ever demonstrated that this enzyme methylates peptides or proteins at a known pre-existing D-aspartyl site.

PIMT may be characterized by its specific activity. One unit of specific activity equals to 1 pmol methyl transferred to $\gamma$-globulin per minute at 30° C., pH 6.0-8.0.

The term "labeling" indicates the use of any marker that, upon methylation of the target carboxyl groups gives a detectable signal. Radiolabeling of the methyl donor S-adenosyl-L-methionine provides a simple radiometric assay for assessing the isoaspartyl content of proteins, and is considered the most convenient, however, the invention is not restricted to radiolabeling. The techniques of forming a detection signal such as via radioactive labeling or chromogenic means using a chromogenic substance as a marker, are well known and documented in the art. [See, for example, Current Protocols in Molecular Biology, Ausubel, et al., Eds., Green Publishing Associates and Wiley-Interscience, 1988].

DESCRIPTION OF PREFERRED EMBODIMENTS

The process according to the present invention, used for the determination of isoaspartate content of proteins, typically includes the following steps:

1. The protein to be analyzed is mixed with a proteolytic enzyme and is incubated under conditions suitable for the operation of the particular enzyme employed. This step breaks the protein into small pieces (peptide fragments) such that the methyltransferase will have free access to all regions of the protein where isoaspartate may reside. The enzymatic digestion is typically performed with trypsin, however, other proteases, such as pepsin, papain, chymotrypsin, etc. can also be used either alone or in suitable combinations with one another. Non-enzymatic methods, such as cyanogen bromide cleavage, may be also used for breaking down the peptide to be analyzed.

2. An inhibitor is added to the reaction mixture to terminate the enzymatic digestion, and to prevent the proteolytic enzyme from degrading PIMT in the next step. If trypsin or chymotrypsin are used in the first step, their action is typically terminated by phenylmethylsulfonyl fluoride (PMSF). Inhibitors for other proteases are well known in the art.

3. The PIMT enzyme is added along with a buffer adjusting the pH of the methylation mixture to the desired value, and AdoMet. If the total isoaspartate content of the analyte protein is to be determined, AdoMet is typically radioactively labeled [$^3$H]AdoMet. However, if the method is used for the assessment of the approximate location of isoaspartate residues within a protein, labeling is not always necessary, since identification of the isoaspartate bearing peptides may be made by observing specific alterations in the behavior of the methylated peptides According to a preferred embodiment, PIMT enzyme having a specific activity comparable to that of the pure enzyme isolated from bovine brain (12-30 nmol/min/mg at 30° C.) should be added such that its final concentration will be at least about 0.5 $\mu$M, preferably about 1-5 $\mu$M. The digested protein should be present typically in a concentration corresponding to about 2-15 $\mu$M intact protein, and the protein to PIMT ratio should typically be kept at or below 4:1, the about 2:1 ratio being considered as optimal.

The AdoMet should typically be present at a total chemical concentration exceeding 10 $\mu$M, and in large excess to the protein. Usually 50-200 $\mu$M AdoMet concentrations are employed.

4. The reaction mixture is incubated. The temperature and time of incubation depend on the protein to be analyzed, and the selection of appropriate methylation conditions for a particular task is well within the knowledge of an ordinarily skilled artisan. During this step, PIMT catalyzes the transfer of the radioactive methyl group from AdoMet onto aspartyl sites of the protein being tested. The methyl groups become covalently attached to the $\alpha$-carboxyl of the isoaspartate via a base-labile methyl ester bond.

5. The reaction is stopped by addition of a suitable alkaline detergent solution, for example, sodium borate, pH 10, containing 2% sodium dodecylsulfate.

6. The mixture is then incubated under specified conditions of temperature and time. During this step, the isoaspartyl methyl esters are hydrolyzed to produce radioactive methanol.

7. The amount of radioactive methanol produced is measured by any of several common techniques, including HPLC, differential solvent extraction, or diffusion/trapping. The latter method is particularly suitable for routine screening.

If the analysis is performed to determine the location of the sites where the isoaspartate has formed, Steps 5-7 may be omitted. In such cases, the reaction mixture from Step 4 is taken, and is subjected to any of several analytical procedures which will produce a high-resolution separation of peptides, for example HPLC or capillary electrophoresis. When using radio-labeled AdoMet as methyl donor, the isoaspartate-containing peptides are identified by collecting the separated peptides individually and assessing the associated amount of radiolabel. The incorporation of radioactive tracer into specific peptides can, for example, be evaluated by HPLC column directly through an on-line radiometric detector.

It may be advantageous to include a reducing agent, such as dithiothreitol, 2-mercaptoethanol, or equivalent, and a mild heating step immediately following the proteolytic step. This serves to break any disulfide bridges and further promote accessibility of PCMT to any isoaspartyl sites. The concentration of the reducing agent, if present, typically is about 1 to 15 $\mu$M.

The practical application of the analytical method disclosed in the present invention can be greatly facilitated by using an analytical kit, typically including:

1. A sterile aqueous reaction solution (buffer) consisting of a pH buffer of appropriate pH and ionic strength, a heavy metal chelator, and a reducing agent.
2. A vial of purified PIMT obtained from any natural source of via recombinant DNA methods.
3. A solution of trypsin or another protease, in a suitable storage solution.
4. A dilution reagent for the protease, which for trypsin typically is a pH buffer and CaCl$_2$.
5. A solution of PMSF or other appropriate protease inhibitor dissolved in isopropanol or another suitable solvent.
6. A solution of unlabeled AdoMet. Before use, this can be mixed in a specified proportion with radioactively labeled [Methyl-$^3$H]AdoMet, which does not need to be included in the kit.

Some of the listed components, for example the reducing agent, heavy metal chelator, are optional.

The invention is further illustrated by the following non-limiting Examples.

EXAMPLE 1

Materials and General Methods

Protropin ® brand of human growth hormone was manufactured by and obtained from Genentech, Inc.

The methylation was performed with type 1 isozyme of protein carboxyl methyltransferase purified from bovine brain as described by Aswad and Deight, *J. Neurochem.* 40, 1718-1725 (1983).

[$^3$H]AdoMet was obtained from Amersham, USA.

EXPERIMENTAL PROCEDURES

Incubations-Recombinant DNA-derived human growth hormones (rhGHs) were dialyzed at 4° C. against 50 mM potassium HEPES, pH 7.4, 1 mM EGTA, 5% glycerol, 0.02% sodium azide. Control portions were frozen at −70° C. immediately after dialysis. Aged portions were placed at 37° C. for varying periods of time as indicated. Incubations were stopped by freezing at −70° C. Incubations of synthetic peptides were performed similarly except that in place of dialysis, the peptides were evaporated from solutions in 0.1% (w/v) trifluoroacetic acid and then resuspended in the aging buffer.

Trypsin Digestions-Aged and control portions of rhGHs (about 2 mg/ml) were dialyzed at 4° C. against 100 mM sodium acetate, 10 mM Tris, 1 mM calcium chloride (pH adjusted to 8.3 with acetic acid). Trypsin that had been treated with L-1-chloro-3-(4-tosylamido)-4-phenyl-2-butanone to remove chymotrypsin activity (Sigma) was then added to give an initial trypsin to hormone ratio of 1:100 (w/w). After 2 h of incubation at 37° C., an amount of trypsin equal to the first was added, and digestion was continued for an additional 2 h. In those cases in which digests were to serve as substrates for protein carboxyl methyltransferase, the digestions were stopped by adding phenylmethylsulfonyl fluoride to a final concentration of 4 mM. Otherwise, digestion was stopped by adding 0.10 volume of 88% phosphoric acid.

High Performance Liquid Chromatography-Reversed-phase HPLC of tryptic fragments was performed using a gradient HPLC system from Gilson and 4.6-mm ×10-cm columns of Aquapore RP-300 (Brownlee Labs) fitted with 3-cm guard columns of the same material. Solvent A was 0.1% (w/v) trifluoroacetic acid in water that was purified using a Milli-Q water system (Millipore). Solvent B was 0.08% (w/v) trifluoroacetic acid in acetonitrile. For some experiments, solvent A was 30 mM sodium phosphate, pH 6.5, and solvent B was acetonitrile. All separations employed a linear gradient of 0.5% solvent B/min and a flow rate of 1 ml/min. Detection at 214 nm was accomplished with a Kratos Spectroflow 757 UV absorbance detector.

Methylation Reactions-Intact growth hormones, purified peptides, or phenylmethylsulfonyl fluoride-stopped trypsin digests were methylated in 40-min, 30° C., pH 6 reactions using the type 1 isozyme of protein carboxyl methyltransferase, which was purified from bovine brain as described previously [Aswad and Deight, *J. Neurochem.* 40, 1718–1725 (1983)]. Reactions were carried out in a final volume in which substrates were present at 10 $\mu$M final concentration, protein carboxyl methyltransferase at 5 $\mu$M (except when protein carboxyl methyltransferase concentration was explicitly varied) and [$^3$H] AdoMet at 200 $\mu$M. The specific activity of protein carboxyl methyltransferase was 15–20 nmol/min/mg at 30° C. when 5 mg/ml $\gamma$-globulin was used as a substrate. The active (S,S)-diastereomer of [$^3$H]AdoMet was present at a specific activity of 80–200 dpm/pmol as determined by the method of Hoffman (1986). Methylation reactions containing intact rhGH were terminated by adding 1 ml of 7% (w/v) trichloroacetic acid, and methyl incorporation was determined according to Aswad and Deight, Supra. Methyl incorporation into purified peptides was determined using a methanol diffusion assay that is a modification of the method of MacFarlane [*J. Biol. Chem.* 259, 1357–1362 (1984)]. Methylation reactions of phenylmethylsulfonyl fluoride-stopped trypsin digests were stopped by freezing at $-15°$ C. They were thawed and immediately injected for reversed-phase HPLC in order to evaluate methyl incorporation into individual fragments.

Amino Acid Compositions—Tryptic fragments (0.2–1 nmol) were collected from reversed-phase HPLC using the trifluoroacetic acid/acetonitrile solvent system. They were then evaporated in acid-washed microcentrifuge tubes by centrifugation under vacuum. HPLC solvent from blank injections was collected in the elution region of each fragment, and these fractions were handled in parallel with the samples. Evaporated samples and blank fractions were resuspended in 0.5 ml of 6 N HCl,0.1% thioglycolic acid and transferred to Pierce Chemical Co. vacuum hydrolysis tubes. After evacuation, the tubes were heated for 24 h at 110° C. in a block heater. The hydrolysates were transferred to fresh acid-washed microcentrifuge tubes, evaporated, resuspended once in fresh water, and evaporated again. They were then resuspended in 20–60 $\mu$l of 2% (w/v) sodium dodecyl sulfate in 0.4 M sodium borate, pH 9.5, evaporated again, and then resuspended in a volume of 12 $\mu$M S-methylcysteine equal to that of the borate solution. The S-methylcisteine served as an internal standard for amino acid composition analysis by the method of Jones et al. (1981), which involves derivatization with o-phthaldialdehyde followed by reversed-phase HPLC and fluorescence detection of the derivatized amino acids. For the separation of amino acid derivatives, a Beckman Ultrasphere ODS C-18 column was used. Detection was accomplished with a Gilson model 121 fluorometer using excitation at 305–395 nm and emission at 430–470 nm. Peak areas of amino acid derivatives in the samples were compared with those from a derivatization of a standard mixture of o-phthaldialdehyde-reactive amino acids (Pierce Chemical Co.). Amino acids were determined in injections containing 25–100 pmol of derivatized hydrolysate. Hydrolyses were performed in duplicate, and results are reported as the means.

Protein Determinations-protein concentrations were determined by the method of Lowry et al. [*J. Biol. Chem.* 193, 265–275 (1951)] following precipitation with 7% (w/v) trichloroacetic acid. Bovine serum albumin was used as a standard.

Results and Discussion

Generation of Isoaspartyl Methylation Sites in Human Growth Hormone

In order to determine whether significant isoaspartate formation would occur in growth hormone at physiological pH and temperature, Met-rhGH was aged for 14 days at pH 7.4, 37° C. It was then assayed for its ability to incorporate methyl groups from bovine brain protein L-isoaspartyl methyltransferase and [$^3$H]AdoMet. The methylaccepting capacity was determined by varying the protein L-isoaspartyl methyltransferase concentration in reactions containing hormone at 10 $\mu$M and [$^3$H]AdoMet at 200 $\mu$M. Under these conditions, the methylation should increase with increasing protein L-isoaspartyl methyltransferase concentration until it reaches a plateau representing complete modification of the isoaspartyl subpopulation that is accessible to the Enzyme (Aswad, D.W. (1984) *J. Biol. Chem.* 259, 10714–10721). As shown in FIG. 2A, a maximal methylation of 0.27 mol of CH$_3$/mol of Met-rhGH was achieved for the aged protein, whereas the control protein could be methylated to no more than 0.01 mol/mol under the same conditions. Maximal methylation was achieved when protein L-isoaspartyl methyltransferase was present at 3 $\mu$M or higher. The requirement for a relatively high enzyme concentration is largely due to the fact that this enzyme has an unusually low turnover number. Several previous studies indicate a similar high protein L-isoaspartyl methyltransferase requirement for stoichiometric methylation of isoaspartyl peptides or deamidated proteins (Aswad, 1984, supra: Johnson, et al., *J. Biol. Chem.* 260, 10913–10916 (1985); DiDonato, et al., supra.

Virtually identical increases in methyl-accepting capacity were observed for different lots of Met-rhGH and for natural sequence rhGH from two manufacturers (Table I). Similar experiments have also been carried out on authentic human pituitary growth hormone (Crescormon ®, KabiVitrum AB). With this material, the methyl-accepting capacity of the untreated material was quite high (0.17 mol of methyl/mol of hormone) probably because the sample available had been stored under uncontrolled conditions for over 2 years. Nevertheless, a 2-week incubation of Crescormon ® under the same conditions used in Table I caused its methyl-accepting capacity to increase to 0.35 mol of methyl/mol of hormone. Although the Crescormon ® samples were not studied further, these results show that the aging-induced formation of isoaspartate is not unique to the recombinant DNA-derived forms of hGH.

TABLE I

Comparisons of aging-induced methyl incorporation into rhGH from various sources
Results are reported as the means of duplicate determinations. The average range of duplicates was 3.1% of the mean for aged samples and 16% of the mean for control samples.

| rhGH | Trade Name | Manufacturer | Methyl incorporation | | |
|---|---|---|---|---|---|
| | | | Control | Aged | Change |
| Met-rhGH[a] | Protropin ® | Genentech | 0.008 | 0.269 | 0.261 |
| Met-rhGH[a] | Protropin ® | Genentech | 0.005 | 0.245 | 0.240 |
| Natural Sequence | | Genentech | 0.004 | 0.249 | 0.245 |
| Natural Sequence | Humatrope ® | Lilly | 0.011 | 0.263 | 0.252 |

[a]Two different lots of Protropin ® were analyzed.

The time course of the generation of isoaspartyl methylation sites in Met-rhGH is shown in FIG. 2B. Methyl incorporation became detectable after 2 days of aging, the earliest time point tested, and it continued to increase over 28 days, approaching 0.5 mol of isoaspartyl methylation sites/mol of polypeptide. The increase in methylation with time was nearly linear in the range studied here, and it proceeded at a rate of 1.8 methyl-accepting sites/day/100 molecules of Met-rhGH. This indicates that hGH is particularly prone to isoaspartate formation. In a recent study, nine proteins were aged under the same conditions used here, and only calmodulin was found to accumulate isoaspartate at a greater rate [Johnson, et al., Arch. Bigchem. Biophys. 268, 276-286 (1989)].

Methyl-accepting Tryptic Fragments of Aged Growth Hormone

As a first step in determining the locations of isoaspartate in aged growth hormone, samples of control and 14-day-aged Met-rhGH were digested with trypsin. The digestion mixtures were either injected directly for reversed-phase HPLC using trifluoroacetic acid-/acetonitrile solvents, or first methylated with protein L-isoaspartyl methyltranferase and [$^3$H]AdoMet and then injected. Peptides were detected by absorbance at 214 nm. Methylated peptides were detected by scintillation counting of collected fractions.

Figure 3A:
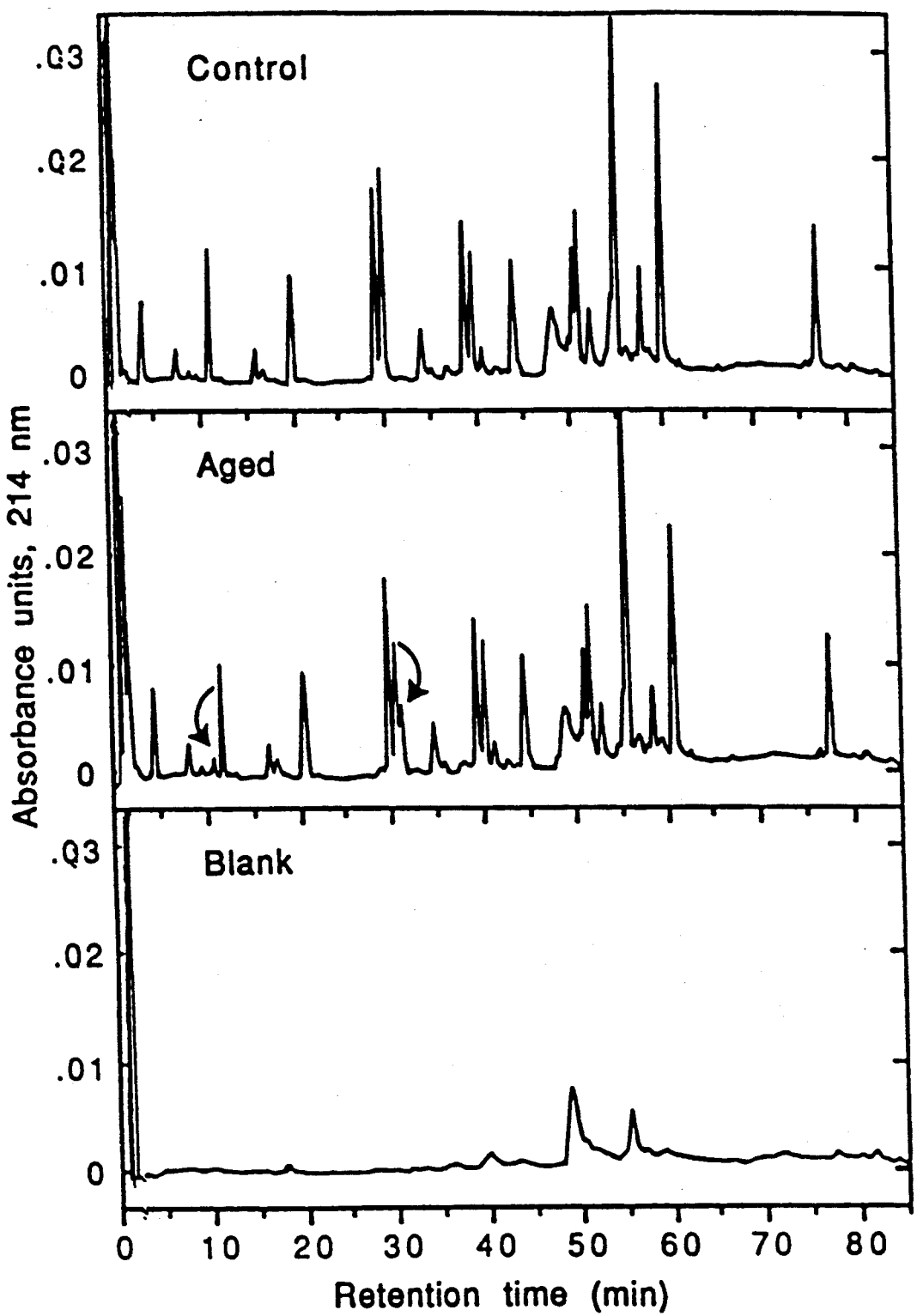
FIG. 3 shows reverse-phase HPLC of tryptic fragments of aged and control Met-rhGH with or without prior methylation by protein carboxyl methyltransferase
Figure 3B:
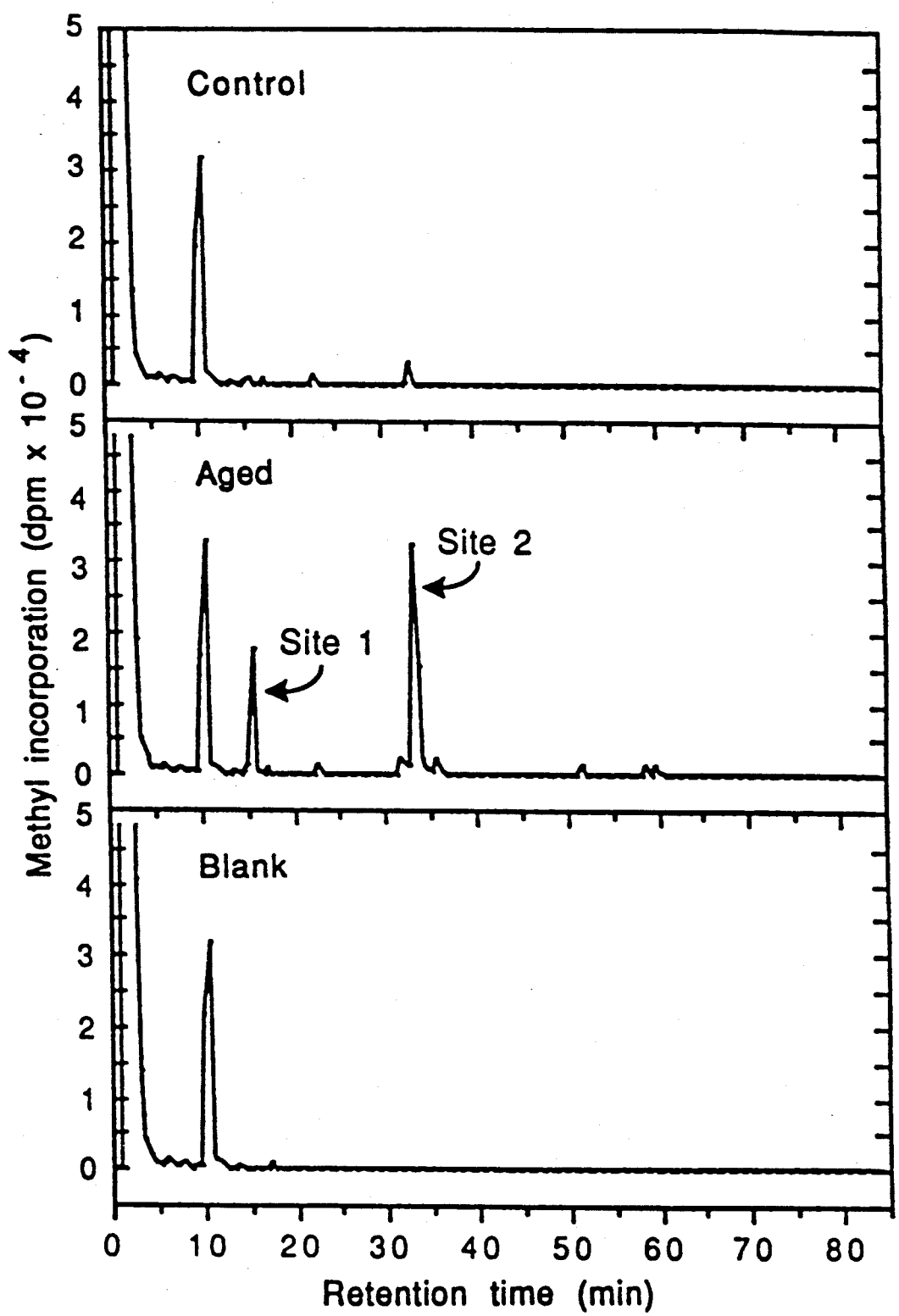

As shown in FIG. 3, right panels, there were two major peaks containing methyl groups when the tryptic digest of aged Met-rhGH was used as a substrate for protein carboxyl methyltransferase. The peaks of radioactive methyl groups were much smaller when the tryptic digest of control Met-rhGH was used as the substrate, indicating that the formation of isoaspartate occurred during the 14-day, pH 7.4, 37° C. aging of the Met-rhGH, not during the trypsin digestion procedure. The first major methylated fragment (site 1) eluted at 15 min and accounted for 22% of the aging-induced methylation recovered from the column. The second major peak of radioactivity (site 2) eluted at 33 min and accounted for 58% of the recovered aging-induced methylation. There were a number of other methylated peptides that were more prevalent after aging of the Met-rhGH. None of these minor methylation sites accounted for more than 5% of the total recovered methyl esters. One minor peak of radioactivity, eluting at 22.5 min, seemed to be attributable to methylation of Met-rhGH, but it did not increase with aging. The sum of these minor peaks made up 20% of the recovered methyl groups.

The total aging-induced methylation of the tryptic fragments recovered from the column represented 0.35 mol of CH$_3$/mol of injected Met-rhGH. This value, when compared with the 0.26 mol of CH$_3$/mol of change in methyl incorporation obtained for the intact protein, suggests that all of the methyl-accepting capacity of the intact Met-rhGH can be accounted for by the methylated fragments recovered from the column. The higher methyl-accepting capacity of the tryptic digest may indicate that some of the isoaspartate generated in the intact hormone was not accessible to the enzyme due to conformational constraints.

Such an effect has been observed in a more extreme form during studies on the methylation of isoaspartate in deamidated bovine seminal ribonuclease (Gallett, et al., (1988b) in Post-translational Modifications of Proteins and Ageing, pp. 229-245,Plenum Publishing Corp., New York).

Each of the two major methylated fragments eluted shortly after a peptide that changed elution position in an aging-dependent manner (indicated by arrows in the center left panel of FIG. 3). Because methylation of a carboxyl group increases the hydrophobicity of a peptide and thus causes later elution during reversed-phase HPLC (Murray and Clarke, J. Biol. Chem. 259, 10722-10732 (1984); Aswad, et al., Biochemistry 26, 657-681 (1987); Johnson, et al., J. Biol. Chem. 262, 5622-5629 (1987b); McFadden and Clarke, J. Biol. Chem. 261 11503-11511 (1986); Galletti, et al., Biochemistry 27, 1752-1757 (1988a)), these altered fragments probably contain the isoaspartates formed during aging. The changes in these two tryptic fragments are the only large differences between control and aged Met rhGH which are apparent from the profile of absorbance at 214 nm. Thus, the formation of isoaspartate may be the major covalent alteration of rhGH occurring under physiological conditions.

In order to test the possibility that the amino-terminal methionine of Met rhGH affected the rate of formation of isoaspartate at any of the sites, the above experiments were repeated with natural sequence rhGH. The methylated peaks in aged natural sequence rhGH were found to be identical in position and relative amounts to those in aged Met rh-GH (not shown). Absorbance profiles in trypsin digests of control and aged natural sequence rhGH also showed the same aging-dependent shifts in the elution of peptide fragments as did Met rhGH.

Isolation and Characterization of Methyl-accepting Site

The fragment that eluted at 12 min in digests of control Met rhGH was decreased in area upon aging of the Met rhGH, and there was a peak at 11.2 min in digests of aged Met rhGH which was not present in digests of the control material (FIG. 3). Methylated site 1 eluted slightly later than this altered fragment, suggesting that the 11.2-min peak may be the isoaspartyl peptide responsible for site 1. To verify that the 11.2-min peak was the methyl acceptor and not some other peptide preceding methylated site 1, 13 nmol of aged Met rhGH was digested with trypsin and injected for reversed-phase HPLC using trifluoroacetic acid/acetonitrile solvents. Each peptide fragment eluting before 15 min was collected, reduced to dryness by centrifugation under vacuum, and resuspended in 150 μl of water. Samples of 25 μl each were then assayed for methyl-accepting capacity. As shown in Table II, only the aging-induced peak eluting at 11.2 min exhibited appreciable methyl incorporation.

TABLE II

Methyl incorporation into peptides
eluting before methylated site 1 in aged Met-rhGH

| Retention Name | Incorporation |
| --- | --- |
| min | pmol CH$_3$/25 μl |
| 8.5 | 2.9 |
| 10.2 | 0.3 |
| 10.8 | 1.6 |
| 11.2 | 117.8 |
| 12.0 | 5.4 |

Figure 4:
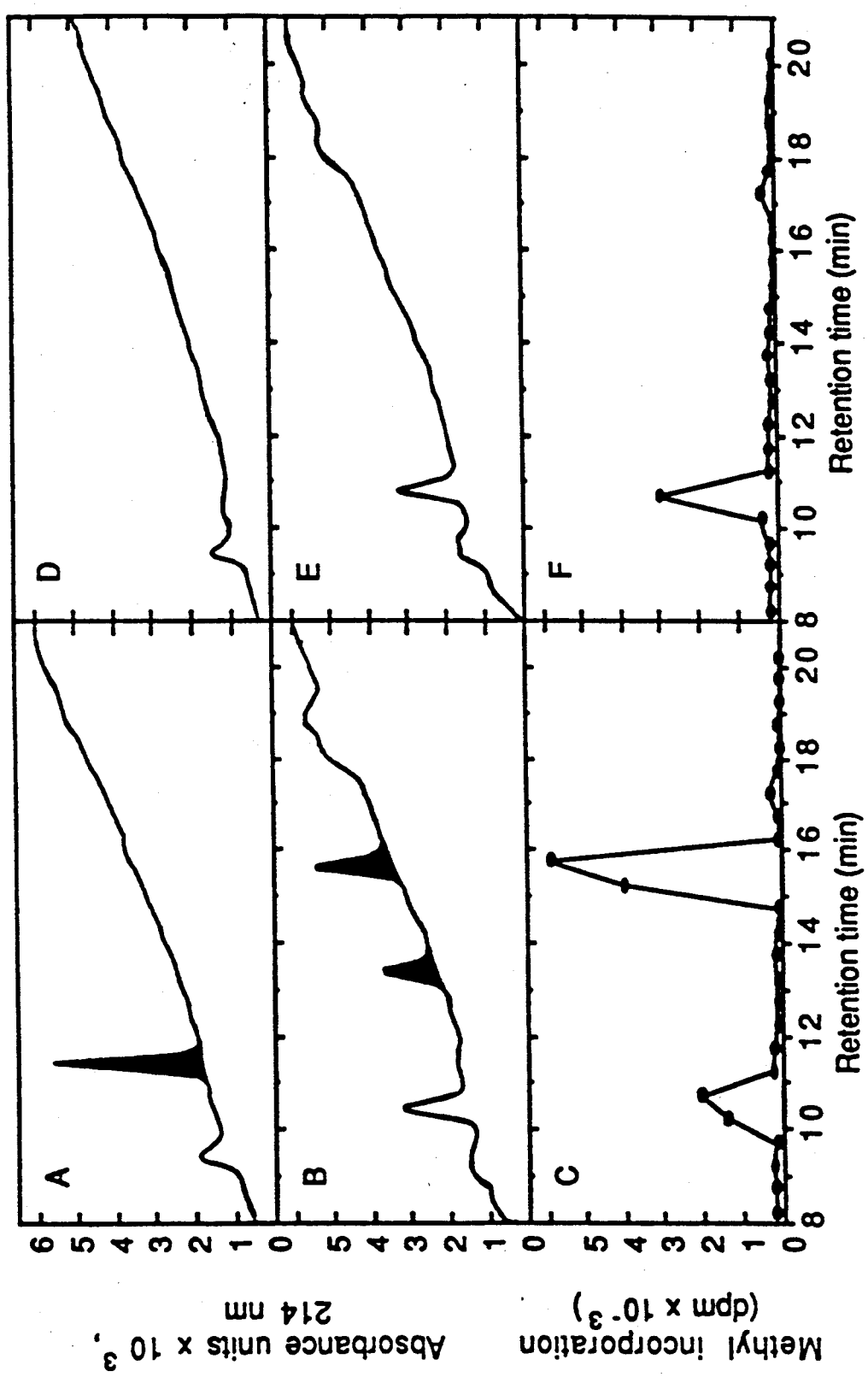
FIG. 4 illustrates the reversed-phase HPLC of purified methyl-accepting site 1.

When the purified 11.2-min peptide was injected for HPLC following methylation by protein carboxyl methyltransferase and [$^3$H]AdoMet, the radiolabeled methyl ester eluted at the same retention time as methylated site 1 (FIG. 4). Therefore, the 11.-2 min peptide did indeed contain methyl-accepting site 1. FIG. 4 also shows that methylation resulted in a complete loss of the original peptide, which indicates that it was quantitatively methylated by protein L-isoaspartyl methyltransferase. The methylated product contained 1.06 mol of CH$^3$/mol of peptide (the amount of peptide was calculated from the absorbance of the methylated peptide at 214 nm relative to the absorbance of the 12-min peptide in an injection of a trypsin digest of 1 nmol of control Met rh-GH). Methylation of the 11.2-min peptide also resulted in the formation of a UV-absorbing unlabeled peak eluting at 13.5 min (FIG. 4B). This peak is probably the cyclic imide intermediate that occurs during nonenzymatic demethylation of methylated isoaspartate [(Johnson and Aswad, *Biochemistry* 24, 2581-2586 (1985)]. Imide-containing peptides generally elute between isoaspartyl peptides and their methyl esters under the HPLC conditions used here (Aswad, et al., *Biochemistry* 26, 675-681 (1987); Johnson, et al., supra (1987b)).

The purified methyl-accepting site 1 was subjected to acid hydrolysis, and its amino acid composition was determined using precolumn derivation with o-phthaldialdehyde followed by reverse-phase HPLC [Jones, et al, *J. Liq. Chromatogr.* 4, 565-586 (1981)]. The 12-min peak, which decreased in area upon aging (see above), was also subjected to amino acid composition analysis. The compositions of the two peptides were identical (Table III) and identified them as the tryptic fragment known to be produced upon digestion of Met rh-GH [Kohr, et al., *Anal. Biochem.* 122, 348-359(1982)]. This fragment contains residues 128-134 of natural sequence hGH, and it has the sequence Leu-Glu-Asp-Gly-Ser-Pro-Arg.

Figure 5:
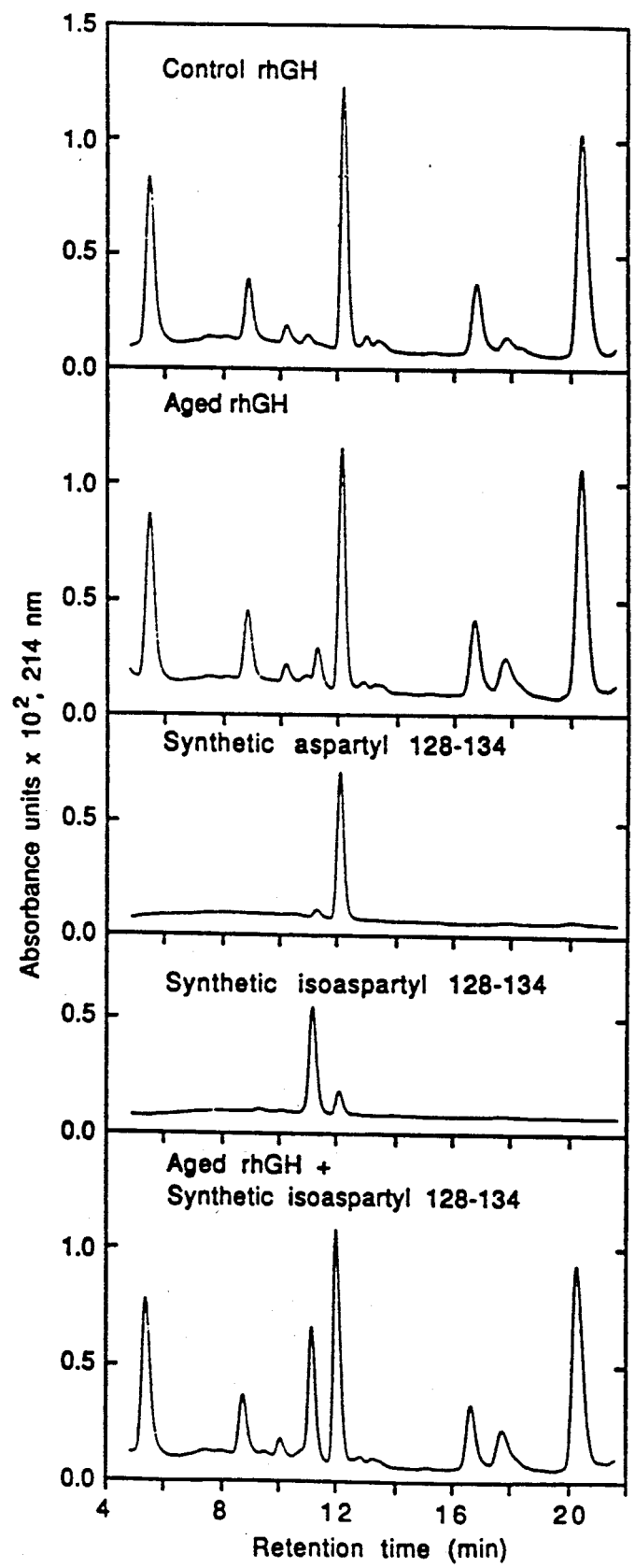
FIG. 5 shows the coelution of methyl-accepting site 1 with synthetic Leu-Glu-isoAsp-Gly-Ser-Pro-Arg.

Because Asp-130 is the only site capable of forming isoaspartate in this fragment, it was concluded that the isoaspartate in site 1 was produced by isomerization of Asp-130 in the intact growth hormone. The identity of methyl-accepting site 1 as Leu-Glu-isoAsp-Gly-Ser-Pro-Arg was further strengthened by synthesizing this peptide and showing that it coeluted exactly with the 11.2-min peak present in trypsin digests of aged rhGH (FIG. 5).

Isolation and Characterization of Methyl-accepting Site 2

Figure 6:
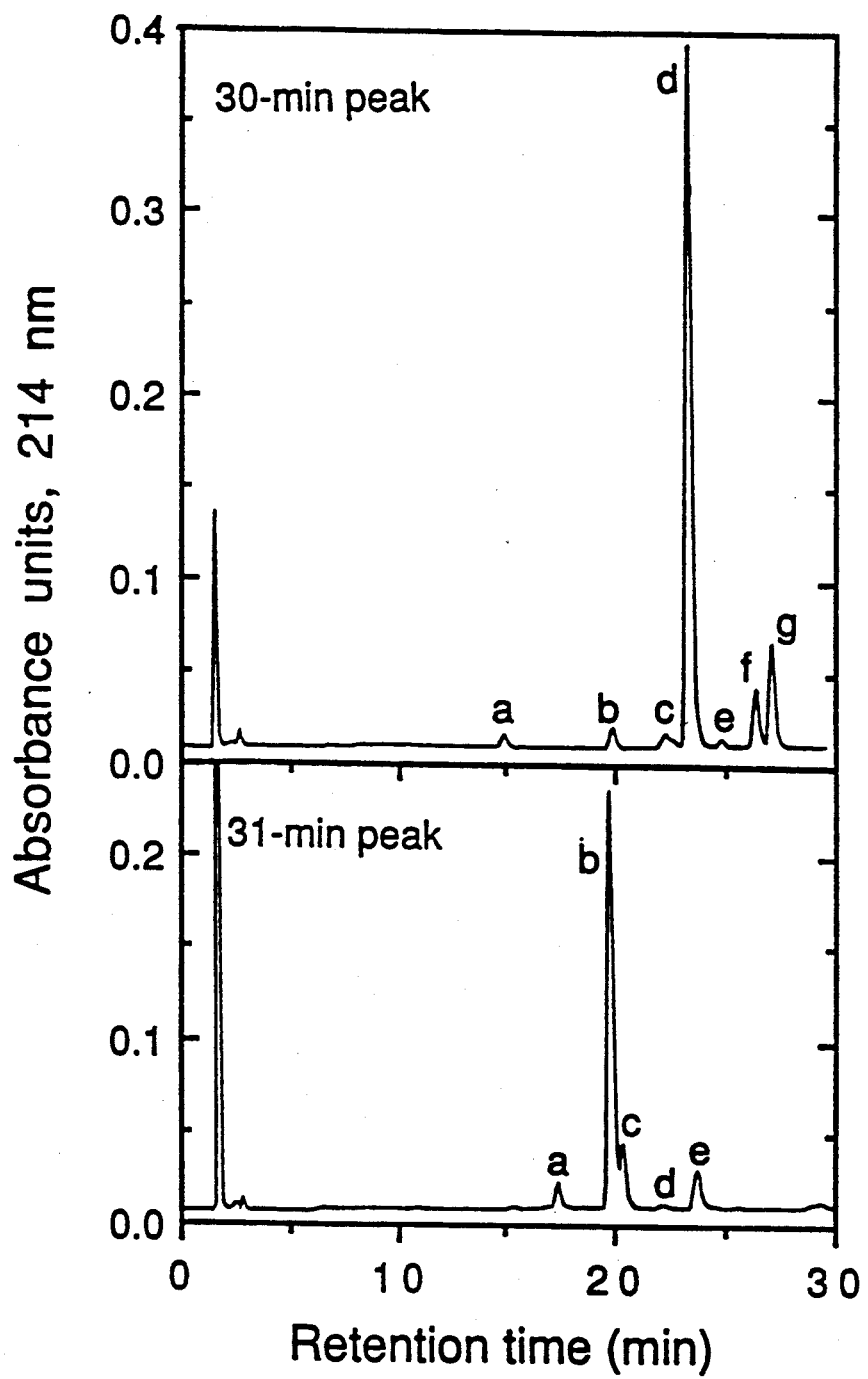
FIG. 6 shows the reversed-phase HPLC using a pH 6.5 solvent system for purification of methyl-accepting site 2.

The fragment of control Met rhGH eluting at 30 min was decreased in size and the digest of aged Met rhGH, and the digest of aged Met rhGH contained a new peak eluting at 31 min (FIG. 3). Methylated site 2 eluted slightly later than this aging-induced peptide (FIG. 3), suggesting that the 31-min peak may contain the isoaspartate responsible for methylated site 2. In order to verify this, the three peaks (29, 30, and 31 min) eluting prior to methylated site 2 were collected from the same 13-nmol injection of aged Met rhGH trypsin digest which was used for characterization of site 1. Because of the extensive overlap between the 30- and 31-min peaks (see FIG. 3), they were further purified by reversed-phase HPLC using 30 mM sodium phosphate, pH 6.5, acetonitrile solvents. FIG. 6 shows that there were one major peptide and a number of minor peptides present in each of the two peaks collected from the trifluoroacetic acid/acetonitrile solvent system. The peak eluting at 29 min in the trifluoroacetic acid/acetonitrile solvents eluted as a single peak in the pH 6.5 solvent system and was therefore not purified further.

TABLE III

Amino acid composition of methyl-accepting site 1

| Residue | 11.2-min peak | 12.0-min peak | hGH (128-134)[a] |
| --- | --- | --- | --- |
| Ala | 0.0 | 0.0 | 0 |
| Arg | 1.0 | 0.7 | 1 |
| Asx | 1.0 | 1.2 | 1 |
| Gly | 0.9 | 0.6 | 1 |
| Glx | 1.0[b] | 1.0[b] | 1 |
| His | 0.1 | 0.0 | 0 |
| Ile | 0.0 | 0.0 | 0 |
| Leu | 1.0 | 1.2 | 1 |
| Lys | 0.0 | 0.1 | 0 |
| Met | 0.0 | 0.0 | 0 |
| Phe | 0.0 | 0.0 | 0 |
| Ser | 0.9 | 0.8 | 1 |
| Thr | 0.0 | 0.0 | 0 |
| Val | 0.0 | 0.0 | 0 |

Each of the peaks observed during reversed-phase HPLC at pH 6.5 was collected, evaporated by centrifugation under vacuum, and resuspended in 150 μM of water. Samples of 25 μl were then assayed for methyl-accepting capacity. The most abundant peptide in the 31-min trifluoroacetic acid/acetonitrile HPLC peak (peptide 31-b) contained the majority of the isoaspartyl methyl-accepting sites (Table IV), making it a good candidate for methyl-accepting site 2. The other minor methyl-accepting peptides that were separated from the major substrate by reversed-phase HPLC at pH 6.5 (Table IV) may represent isoaspartyl peptides responsible for the two minor peaks of methylation eluting adjacent to site 2 (FIG. 3).

TABLE IV

Methyl incorporation into peptides eluting before
methylated site 2 in aged Met-rhGH

| Peptide | Incorporation pmol CH$_3$/25 μl |
| --- | --- |
| 29 | 17.5 |
| 30-a | 2.0 |
| 30-b | 0.7 |
| 30-c | 8.0 |
| 30-d | 2.9 |
| 30-e | 5.5 |
| 30-f | 2.4 |
| 30-g | 3.7 |
| 31-a | 14.2 |
| 31-b | 119.5 |
| 31-c | 20.3 |
| 31-d | 3.7 |
| 31-e | 4.0 |

Figure 7:
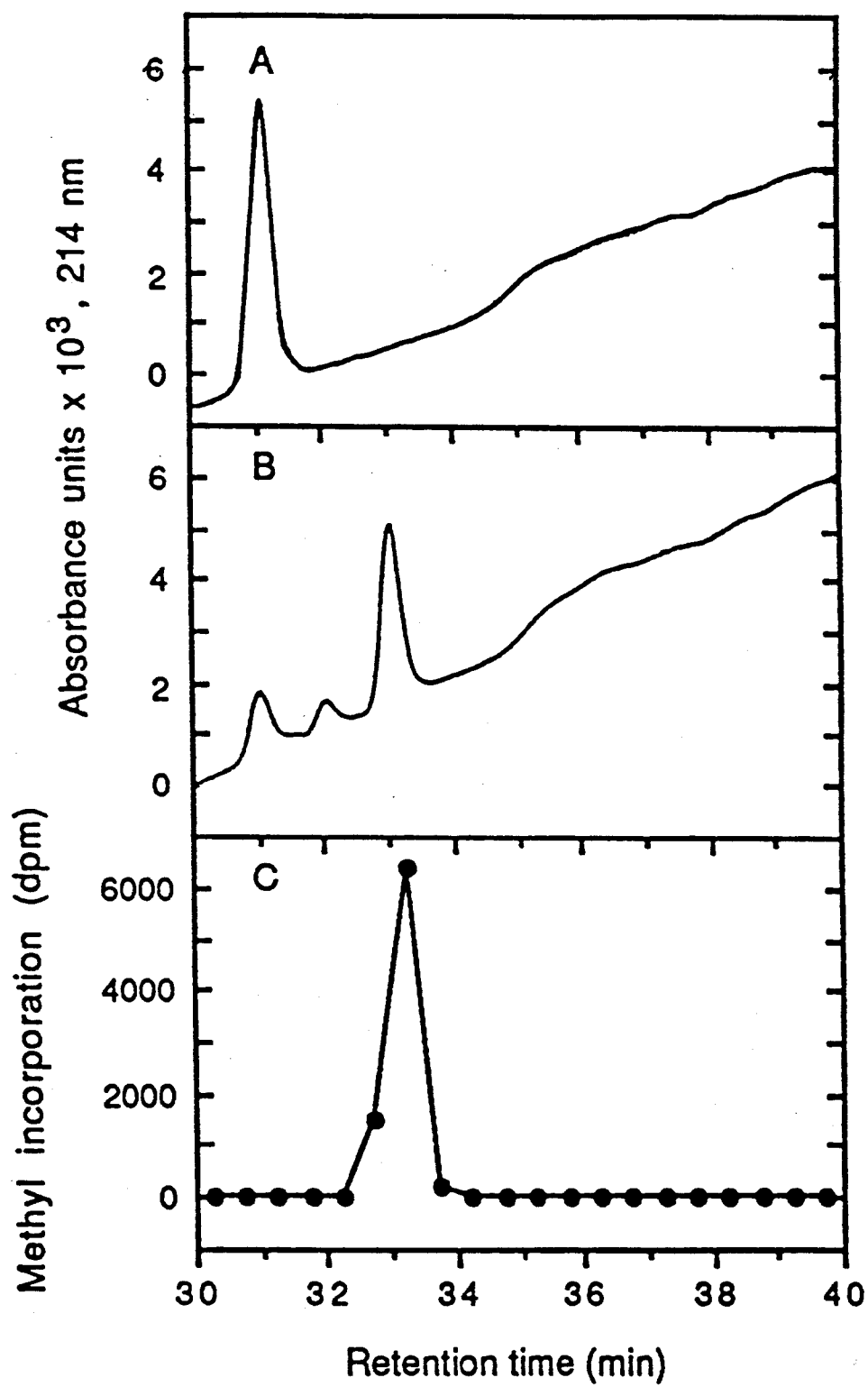
FIG. 7 illustrates the reversed-phase HPLC of purified methyl-accepting site 2.

When purified isoaspartyl peptide 31-b was methylated with protein carboxyl methyltransferase and [$^3$H]AdoMet and then injected for reverse-phase HPLC using trifluoroacetic acid/acetonitrile solvents, the methyl ester eluted with exactly the same retention time as methylated site 2 (compare FIG. 7 with FIG. 3). The methylated product contained 0.67 mol of CH$_3$/mol of peptide, suggesting a single methyl-accepting site (the amount of peptide was calculated from the absorbance of the methylated peptide at 214 nm relative to the absorbance of the 30-min peptide in an injection of trypsin digest of 1 nmol of control Met rh-GH). Methylation of isoaspartyl peptide 31-b also resulted in the formation of an unlabeled peak eluting at 31 min (FIG. 7B). This peak is probably the cyclic imide intermediate produced during the demethylation of methylated site 2. A comparison of peaks A and B in FIG. 7 indicates that methylation of 31-b was not stoichiometric. We believe that the residual material seen at 31 min in band B is the result of an asparagine to aspartate conversion at succinimide-prone asparagine sites [Bornstein and Balian, *Methods Enzymol.* 47, 132–145 (1977); Blodgett, et al., *J. Am. Chem. Soc.* 107, 4305–4313 (1985)]. Indeed, Edman degradation of peptide 31-b (discussed later) indicates that about 20–30% of 31-b contains a normal aspartic acid at position 149.

In order to identify peptides 31-b and 30-d, they were subjected to reverse-phase HPLC using trifluoroacetic acid/acetonitrile solvents, dried, and then subjected to 24-h hydrolysis in 6 N HCl at 110° C. in preparation for amino acid composition analysis. Table V shows that the compositions of isoaspartyl peptide 31-b and peptide 30-d were identical and identified the fragments as residues 146–158 of natural sequence hGH, which has the sequence Phe-Asp-Thr-Asn-Ser-His-Asn-Asp-Asp-Ala-Leu-Leu-Lys. This tryptic fragment has been observed previously upon digestion of Met rhGH (Kohr, et al., supra (1982)).

TABLE V

| Amino Acid composition of methyl-accepting site 2 | | | |
|---|---|---|---|
| Residue | 30-min peak | 31-min peak | hGH(146–158) |
| Ala | 0.8 | 0.9 | 1 |
| Arg | 0.1 | 0.0 | 0 |
| Asx | 4.7 | 4.7 | 5 |
| Gly | 0.0 | 0.0 | 0 |
| Glx | 0.0 | 0.1 | 0 |
| His | 0.7 | 0.7 | 1 |
| Ile | 0.0 | 0.0 | 0 |
| Leu | 2.3 | 2.1 | 2 |
| Lys | 0.3 | 0.3 | 1 |
| Met | 0.0 | 0.0 | 0 |
| Phe | 1.2 | 1.2 | 1 |
| Ser | 0.7 | 0.7 | 1 |
| Thr | 1.0$^a$ | 1.0$^a$ | 1 |
| Val | 0.0 | 0.0 | 0 |

$^a$Values are normalized to 1.0 threonine/peptide.

There are 2 asparagines and 3 aspartates present in the 146–158 fragment, and therefore the position of the isoaspartyl linkage was not obvious from simply identifying the peptide. The relative elution positions of isoaspartyl peptide 31-b and peptide 30-d in both the pH 6.5 and trifluoroacetic acid/acetonitrile solvent systems were consistent with the identify of isoaspartyl peptide 31-b as a deamidated version of peptide 30-d. Because the side chain carboxylic acid of isoaspartate bears a negative charge at pH 6.5, it should be less hydrophobic than the side chain amide of asparagine. A peptide containing isoaspartate in place of asparagine should therefore elute earlier upon reversed-phase HPLC at this pH. Indeed, in the pH 6.5 solvent system, isoaspartyl peptide 31-b eluted earlier than peptide 30-d (FIG. 6). During trifluoroacetic acid/acetonitrile reversed-phase HPLC performed on the column used in these experiments, synthetic isoaspartyl peptides elute slightly later than the corresponding asparaginyl peptides (Johnson, et al, (1987b)), and isoaspartyl peptide 31-b eluted later than peptide 30-d (FIG. 3).

Figure 8:
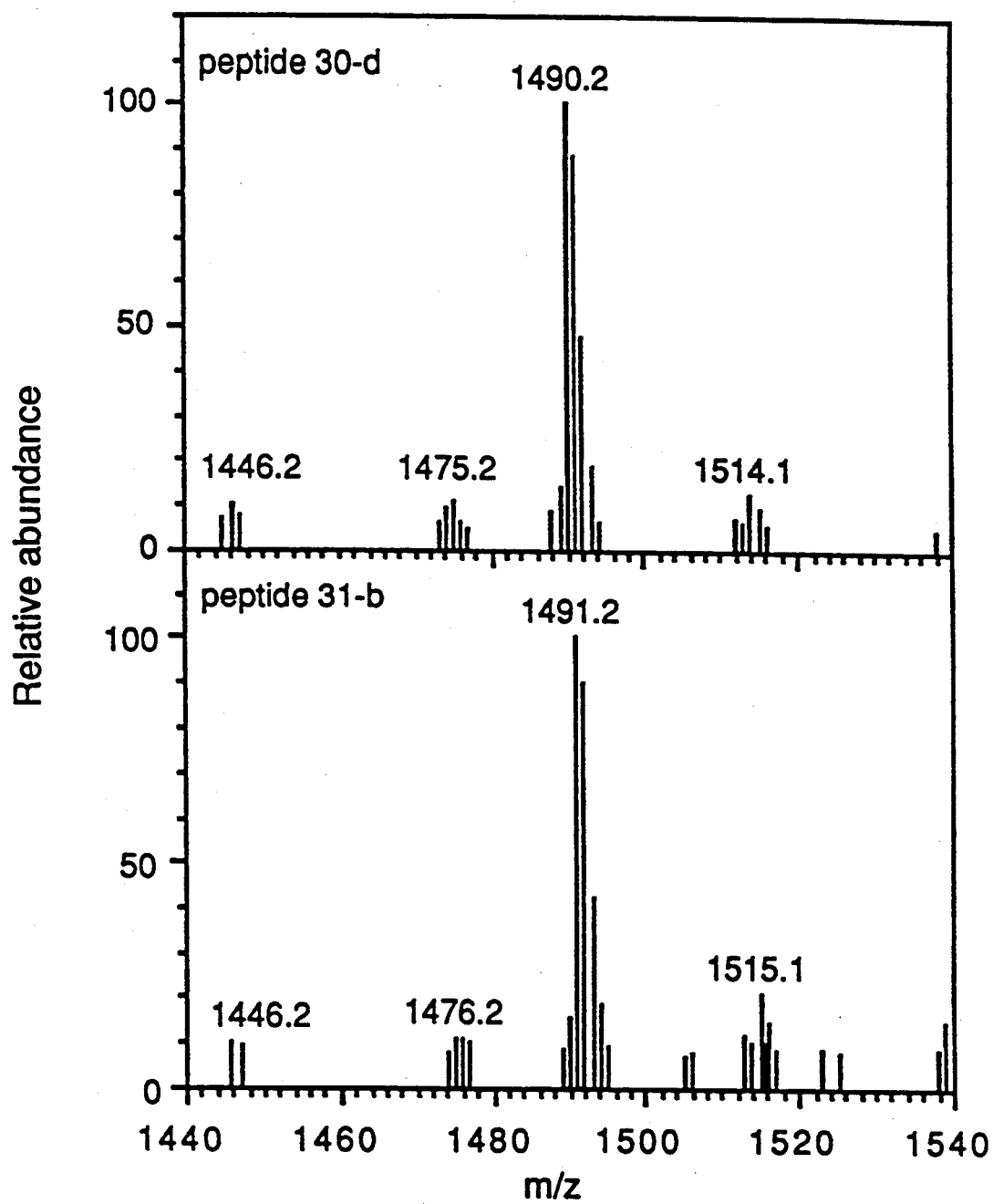
FIG. 8 illustrates a mass spectrum of native and isoaspartyl versions of the 146-158 tryptic fragment from aged Met-rhGH.
Figure 9A:
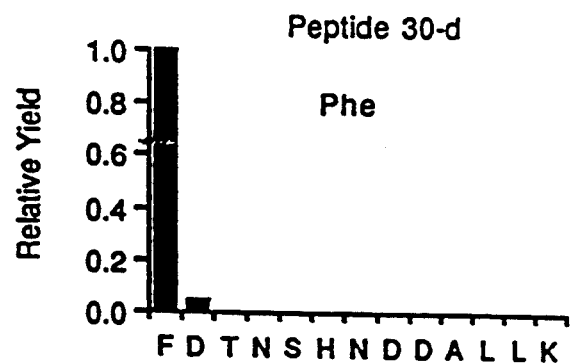
FIG. 9 shows the automated Edman degradation of the 146-158 tryptic peptides from native (30-d) and aged (31-b) Met-rhGH.
Figure 9B:
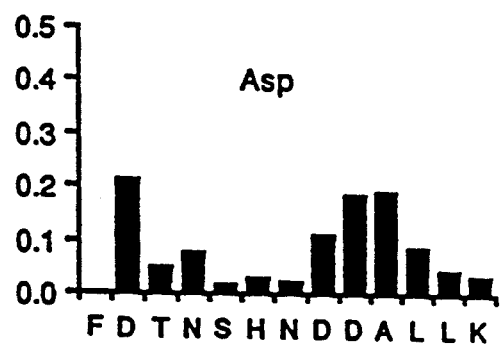
Figure 9C:
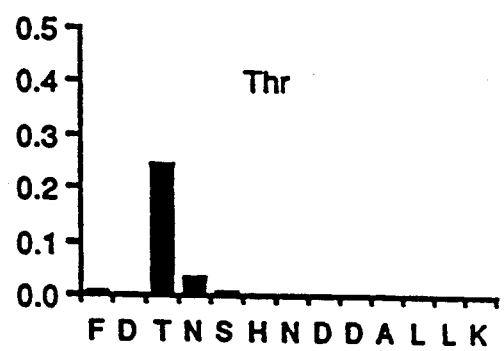
Figure 9D:
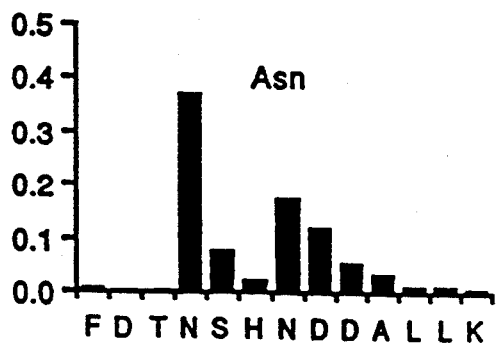
Figure 9E:
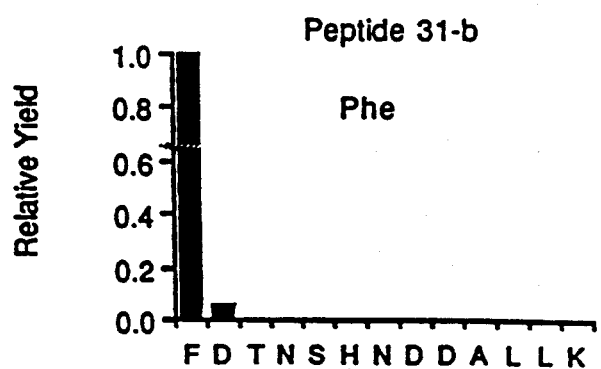
Figure 9F:
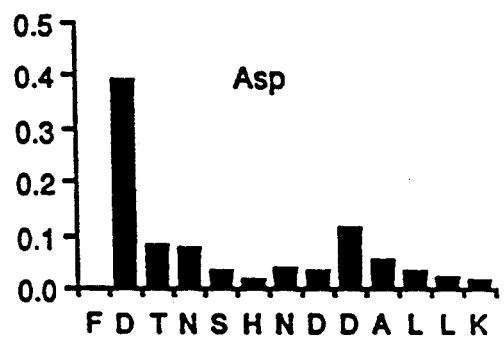
Figure 9G:
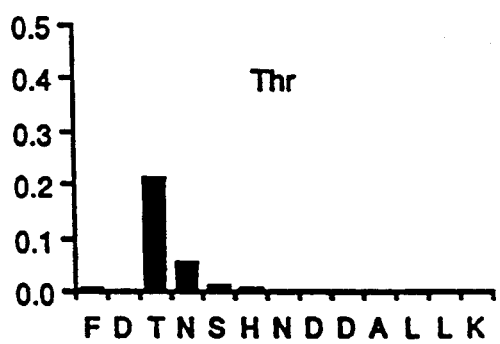
Figure 9H:
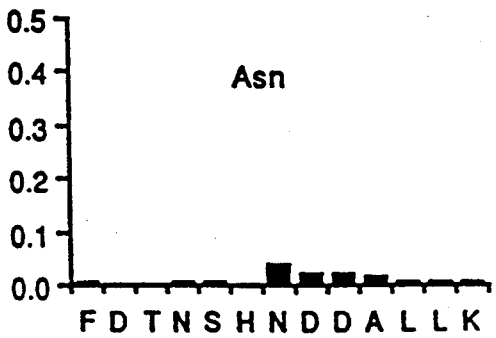

In order to establish further the possibility that isoaspartyl peptide 31-b was a deamidated form of peptide 30-d and to determine the number of deamidation sites, peptides 31-b and 30-d were subjected to fast atom bombardment mass spectrometry. Deamidation of a single asparagine residue should result in an increase of 1 atomic mass unit, because NH$_2$, which has a monoisotopic mass of 16, becomes replaced with OH, which has a mass of 17. The mass expected for the 146–158 peptide is 1489.69 atomic mass units. The positive ion spectra in the molecular ion region for peptide 30-d and isoaspartyl peptide 31-b are shown in FIG. 8. The most abundant ion that was observed for peptide 30-d in the region 1470–1520 m/z Was 1490.2. The peptide 31-b, the most prominent ion was 1491.2 m/z. These results suggest that isoaspartyl peptide 31-b is a monodeamidated version of the 146–158 peptide.

The location of the deamidated asparagine was detected by automated Edman degradation. FIG. 9 shows the yields of phenylalanine, aspartic acid, threonine, and asparagine through all 13 sequencing cycles with both peptides. In peptide 31-b, no significant asparagine was detected at position 149 (cycle 4), but considerable asparagine was detected at position 152 (cycle 7). The lower relative yield of Asn-152 in peptide 31-b relative to peptide 30-d is expected if one assumes that deamidation of Asn-149 results in a mixture of 75–80% isoaspartate and 20–25% aspartate as suggested earlier in FIG. 7. Edman sequencing fails at isoaspartate (Smyth, et al., (1962) *J. Biol. Chem.* 237, 1845–1850) but will continue for that portion of the peptide in the aspartyl form. Indeed, the average yields of amino acids in positions 150–158 in peptide 31-b were approximately one-fourth of the corresponding yields obtained with 30-d (data not shown). Most importantly, there was no additional drop in relative yield associated with positions 153/154, suggesting the absence of any significant isomerization at these two aspartates. Taken together, the HPLC patterns (FIG. 7), mass spectroscopy data, and the sequencing results are consistent with the hypothesis that site 2 has a single major methylation site associated with the formation of isoaspartate arising via deamidation of Asn-149.

A previous study reported that the major site of asparagine deamidation in hGH was Asn-152 [Lewis, et al., *J. Biol. Chem.* 256, 11645–11650(1981)]. The same study suggested that deamidation of Asn-152 prevented cleavage by subtilisin of the Asn-Ser bond at positions 149–150 [Lewis, et al., *Biochem. Biophys. Acta* 214, 498–508 (1981)]. Our results suggest another explanation for the altered cleavage of the deamidated hGH: the presence of an isoaspartyl linkage between Asn-149 and Ser-150. The failure of most proteases to cleave isoaspartyl bonds is well documented [Dorer, et al., *Arch. Biochem. Biophys.* 127, 490–495 (1968); Pisano, et al., *Arch. Biochem. Biophys.* 117, 394–399 (1960); Haley, et al., *Biochemistry* 5, 3229–3235 (1966); Haley and Corcoran, *Chichemistry* 6, 2668–2672 (1967); Murray and Clarke, *J. Biol. Chem.*, 259, 10722–10732 (1984)]. Our incubations of rhGH at pH 7.4, 37° C., caused deamidation and isoaspartate formation at Asn-149 but apparently little deamidation of Asn-152. The conditions used in the previous study (Lewis, et al., supra (1981)) were somewhat more extreme, employing a pH of 8.3, and they may have resulted in the deamidation of both asparagines with subsequent isoaspartyl bond formation. Recently, a report was published by Becker, et al. *Biotech. Appl. Biochem.*, 10, 326-337 (1988), that incubation of rhGH at 37° C., pH 9, for 72 h resulted in a major site of deamidation at Asn-149 with a minor site at deamidation observed at the Asn-152. This is consistent with our findings. The additional deamidation observed at the Asn-152 is, again, likely due to the higher pH of incubation used by this latter group.

Influence of Growth Hormone Structure on the Rate of isoasoartate Formation at Aso-130 and Asn-149

Asn-159 is followed by serine, a sequence in rhGH, positions 99-100, which did not appear to form isoaspartate during aging, suggesting that the structure of the intact rhGH molecule significantly influences the rate of isoaspartate formation. Differential degrees of deamidation of asparagine in Asn-Ser sequences have also been observed for trypsin [Kossiakoff, *Science*, 240, 191-194 (1988)] and were explained by the differing bond angles that control access of the α-nitrogen of the serine residue to the β-carbonyl of the asparagine and therefore dictate the ease of cyclic imide formation.

Although the crystal structure of hGH has not been determined, a moderate resolution crystal structure has been obtained for porcine growth hormone and the extensive sequence homology between the two hormones allows comparisons to be made [Abdel-Meguid, et al., *Proc. Natl. Acad. Sci. U.S.A.* 84, 6434-6437 (1987)]. In the porcine hormone, the stretch of amino acids spanning positions 128-151 is remarkable for its lack of well defined structure (Abdel-Meguid, et al., supra (1987)). Hence, there may be considerable freedom of rotation around the peptide backbone in this region, and imide formation may occur easily. This may explain the susceptibility of Asp-130 and Asn-149 to isoaspartate formation. The site in porcine growth hormone corresponding to the Asn-Ser sequence at positions 99-100 in rhGH lies in a short fold between two of the four helices in the molecule (Abdel-Meguid, et al., supra (1987)). This region of the molecule might be expected to be more constrained in its movement, thus preventing imide formation We were interested in determining the effect of rhGH structure on the amount of isoaspartate formation at Asp-130 and Asn-149. We therefore aged synthetic peptides corresponding to the native 128-134 and 146-158 tryptic fragments under the same conditions that had been used for intact rhGH. Isomerization and deamidation to isoaspartate were evaluated by reversed-phase HPLC in trifluoroacetic acid/acetonitrile solvents. When the synthetic 128-134 peptide was aged for 14 days at pH 7.4 and 37° C., 16% of the material shifted from 12 to 11.2 min, the elution position of the isoaspartyl peptide. In intact 14-day, pH 7.4, 37° C. aged Met rhGH, 14% of the 128-134 fragment was present as the isoaspartyl 11.2-min peak (FIG. 5). Therefore, the isomerization of Asp-130 occurred only slightly faster in the small peptide than in the intact rhGH molecule These extents of degradation correspond to estimated half-lives of 55.6 and 64.3 days for Asp-130 in the synthetic peptide and the intact hormone, respectively. It is interesting to compare these numbers with the data of Geiger and Clarke *J. Biol. Chem.* 262, 785-794 (1987), who found that a peptide with the sequence Val-Try-Pro-Asp-Gly-Ala, i.e., with a similar Asp-Gly bond, exhibited a half-life of 53 days when aged in vitro at the same pH and temperature. It appears that the Asp-Gly sequence has an inherent half-life of about 53-56 days and that Asp-130 in the intact hormone is in a domain that has a conformational flexibility similar to that of a short synthetic peptide.

Figure 10:
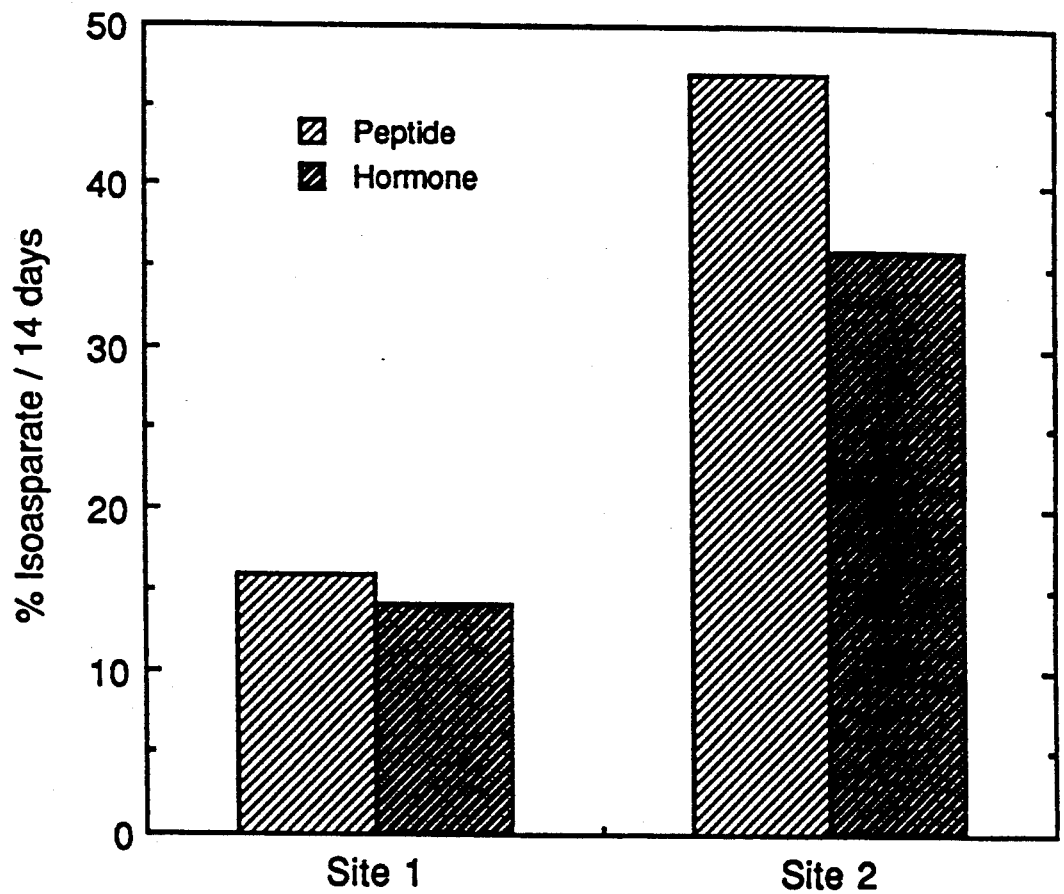
FIG. 10 illustrates the rates of isoaspartate formation at sites 1 and 2 in Met-rhGH compared with the rates of isoaspartate formation in the synthetic peptides corresponding to these sites.

When the synthetic 146-158 peptide was aged for the same period of time under the same conditions, 47% of the material shifted to 31 min, the position of the isoaspartyl peptide. In aged Met rh-GH, 36% of the 146-158 peptide was present in the 31-min isoaspartate-containing peptide (FIG. 3). Thus, the rate of deamidation of this peptide was about 50% faster than deamidation in the intact molecule. These results are summarized in FIG. 10. It appears, in this instance at least, that protein structure has an effect on the rate of isoaspartate formation, and the sites that will produce isoaspartate in an intact protein cannot be predicted on the basis of amino acid sequence alone. Bond angles in structured domains of proteins tend to form a large barrier to cyclic imide formation [Clarke, (1987) supra: Kossiakoff, (1988) supra]. It is therefore likely that most isoaspartate formation occurs in relatively unstructured domains of intact proteins or in domains susceptible to transient unfolding, so that sequence considerations can come into play.

EXAMPLE 2

Determination of Isoaspartate in Native and Aged Calmodulin

Methods

Digestion of samples with trypsin —250µl of calmodulin (2.0 mg/ml, in 50 mM potassiun-HEPES [4-(2-hydroxyethyl]-1-piperazineethanesulfonic acid), 1.0 mM EGTA ([ethylenebis(oxyethylenenitrilo)]tetracetic acid), 0.02% sodium azide, pH 7.4) is combined in a microfuge tube with 3.0 µl of trypsin (11.8 mg/ml in 1.0 mM HCl) and incubated at 37° C. for 2 hr. An additional 3.0 µl of trypsin is then added and the incubation is continued for an additional 2 hr. The digestion is stopped by adding 10 µl of phenylmethylsulfonyl fluoride (PMSF; 0.1 M in isopropanol).

Methylation of tryptic digest—2 µl of the digested calmodulin (as above) is enzymatically methylated via the PIMT reaction in a final volume of 50 µl. The methylation reaction is carried out in the pH 6.2 phosphate-citrate-EDTA buffer of Kim, et al. [*Anal. Biochem.* 84:415-422 (1987)] with 5 µM PIMT and 200 µM [$^3$H-methyl]AdoMet, ca. 400 dpm per pmol. Just before use, the labeled AdoMet is dried in a vacuum centrifuge and resuspended in the original volume of water, in order to remove any volatile label in the AdoMet stock solution. The reaction is initiated by addition of the labeled AdoMet in a volume of 10 µl. After incubation at 30° C. for 40 min., the reaction is stopped by adding 50 µl of alkaline stop solution (0.4 M sodium borate, pH 10, 4% (w/v) sodium dodecylsulfate, 2% (v/v) methanol).

Methanol diffusion assay—50 µl of the stopped methylation reaction is immediately spotted onto a piece of Whatman 3MM filter paper lodged in the neck of a glass scintillation vial that contains 8 ml. of liquid scintillation fluid. The vial is capped and incubated at 40° C. for 2 hrs. The paper is then removed and the vial counted in a liquid scintillation counter. The amount of radiolabel detected is directly proportional to the amount of isoaspartate in the protein digest.

| sample analyzed | Results: cpm | mol methyl[a] / mol protein |
|---|---|---|
| trypsin blank[b] | 893 ± 78 | |
| native calmodulin | 1512 ± 111 | 0.032 ± .002 |
| aged calmodulin[c] | 16870 ± 437 | 0.828 ± .020 |

[a] The values for native and aged calmodulin were calculated after subtracting the trypsin blank.
[b] The blank is a trypsin digest that contains no substrate protein, but is otherwise treated identically to the other samples.
[c] Incubated for 2 weeks at 37° C., pH 7.4 to induce isoaspartate formation.

The foregoing details specific methods for performing the invention. It should be understood, however, that various modifications are possible without deviating from the basic concept of the invention. The invention is intended to include all such modifications and is, by no means, restricted to the examples. The scope of the invention should be determined by the lawful interpretation of the appended claims.

I claim:

1. A method for the quantitative determination of the isoaspartyl content of a polypeptide, comprising the following steps in order:
    breaking said polypeptide into fragments in a reaction mixture with a proteolytic enzyme;
    inhibiting said proteolytic enzyme;
    quantitatively methylating the isoaspartyl residues in said fragments in said mixture with labeled-S-adenosyl-L-methionine in the presence of a protein L-isoaspartyl methyltransferase (PIMT); and
    determining the total amount of methyl groups incorporated into said fragments without previous separation of said fragments from said reaction mixture, via detection of the signal of said label.

2. The method according to claim 1 wherein said PIMT is bovine brain type I PIMT.

3. The method according to claim 2 wherein the specific activity of said bovine brain type I PIMT is at least about 12,000 units/mg.

4. The method according to claim 1 wherein said polypeptide fragments are obtained by digestion with a proteolytic enzyme.

5. The method according to claim 4 wherein said proteolytic enzyme is trypsin.

6. The method according to claim 5 wherein the trypsin digestion is terminated by a trypsin inhibitor.

7. The method according to claim 6 wherein said trypsin inhibitor is phenylmethylsulfonyl fluoride (PMSF).

8. The method according to claim 1 wherein said S-adenosyl-L-methionine is radioactively labeled.

9. The method according to claim 8 wherein the radioactive label is tritium.

10. The method according to claim 1 wherein said PIMT is employed in an amount of at least about 0.5 µM.

11. The method according to claim 10 wherein the amount of PIMT is between about 1 and about 5 µM.

12. The method according to claim 10 wherein the ratio of said polypeptide to said PIMT is up to about 4:1.

13. The method according to claim 12 wherein said ratio is about 2:1.

14. The method according to claim 1 wherein said methylation is carried out at a pH of between about 6.0 and about 8.0.

15. The method according to claim 14 wherein said pH is about 6.2±0.2.

16. The method according to claim 1 wherein said mixture subjected to methylation contains a reducing agent in a concentration of about 1 to 15 µM.

17. The method according to claim 9 wherein the total amount of the methyl groups incorporated into said polypeptide fragments is determined by hydrolyzing the isoaspartyl methyl esters and determining the amount of radioactive methanol formed.

18. The method of claim 1 wherein said mixture comprises fragments of more than one polypeptide.

19. A method for the assessment of the approximate locations of isoaspartate residues within a protein, comprising the following steps in order:
    a) breaking said protein into fragments in a reaction mixture with a proteolytic agent;
    b) inhibiting the proteolytic activity of said proteolytic agent;
    c) quantitatively methylating the isoaspartyl residues in said fragments of said protein in said reaction mixture with S-adenosyl-L-methionine, without previously separating said fragments from said reaction mixture, in the presence of a protein L-isoaspartyl methyltransferase (PIMT);
    d) separating the fragments of said protein from said reaction mixture; and
    e) identifying the fragments containing isoaspartyl methyl ester residues.

20. The method according to claim 19 wherein said PIMT is bovine brain type I PIMT.

21. The method according to claim 20 wherein the specific activity of said bovine brain type I PIMT is at least about 12,000 units/mg.

22. The method according to claim 19 wherein said polypeptide fragments are obtained by digestion with a proteolytic enzyme.

23. The method according to claim 22 wherein said proteolytic enzyme is trypsin.

24. The method according to claim 23 wherein the trypsin digestion is terminated by a trypsin inhibitor.

25. The method according to claim 24 wherein said trypsin inhibitor is phenylmethylsulf (PMSF).

26. The method according to claim 19 wherein said PIMT is employed in an amount of at least about 0.5 µM.

27. The method according to claim 26 wherein the amount of PIMT is between about 1 and about 5 µM.

28. The method according to claim 27 wherein the ratio of said protein to said PIMT is up to about 4:1.

29. The method according to claim 28 wherein said ratio is about 2:1.

30. The method according to claim 19 wherein said methylation is carried out at a pH of between about 6.0 and about 8.0.

31. The method according to claim 30 wherein said pH is about 6.2±0.2.

32. The method according to claim 19 wherein said mixture subjected to methylation contains a reducing agent in a concentration of about 1 to 15 µM.

33. The method according to claim 19 wherein said fragments are separated by high-performance liquid chromatography (HPLC).

34. The method according to claim 33 wherein said S-adenosyl-L-methionine is radioactively labeled.

35. The method according to claim 34 wherein the incorporation of the radioactive label into the individual fragments of said protein is evaluated through an on-line radiometric detector.

36. A process for the quantitative determination of the isoaspartyl content of a polypeptide, comprising the following steps in order:
   a) digesting said polypeptide with a proteolytic enzyme to produce a reaction mixture containing protein fragments; and
   b) contacting said reaction mixture with S-adenosyl-L-methionine, in the presence of a protein L-isoaspartyl methyltransferase (PIMT), without previously separating said fragments from said reaction mixture in order to methylate the isoaspartyl residues in said fragments.

37. The process according to claim 36 wherein said PIMT is employed in an amount of at least about 0.5 [M.

38. The process according to claim 37 wherein the amount of PIMT is between about 1 and about 5 $\mu$M.

39. The process according to claim 37 wherein the ratio of said polypeptide to said PIMT is up to about 4:1.

40. The process according to claim 39 wherein said ratio is about 2:1.

41. The process according to claim 36 wherein the methylation of said isoaspartyl residues is carried out at a pH of between about 6.0 and about 8.0.

42. The process according to claim 41 wherein said pH is about 6.2±0.2.

43. The process according to claim 36 wherein said reaction mixture contains a reducing agent in a concentration of about 1 to 15 $\mu$M.

44. A method of determining the amount of isoaspartate residues in a polypeptide, comprising the following steps in order:
   breaking said polypeptide into a plurality of polypeptide fragments using a proteolytic agent in a reaction mixture;
   inhibiting the proteolytic activity of said proteolytic agent;
   specifically methylating isoaspartate residues present in said polypeptide fragments with labeled methyl groups without separating said fragments from said reaction mixture; and
   determining the amount of isoaspartate residues in said polypeptide by determining the amount of said labeled methyl groups on said polypeptide fragments.

45. The method of claim 44, wherein said isoaspartate residues are specifically methylated by the PIMT enzyme.

46. The method of claim 45, wherein said PIMT is bovine brain type I PIMT.

47. The method of claim 45, wherein said PIMT is employed in an amount of at least about 0.5 $\mu$M.

48. The method of claim 47, wherein the amount of PIMT in said reaction mixture is between about 1 and about 5 $\mu$M.

49. The method of claim 45, wherein the ratio of said polypeptide to said PIMT is up to about 4:1.

50. The method of claim 49, wherein said ratio is about 2:1.

51. The method of claim 44, wherein the methylation of said isoaspartate residues is carried out at a pH o between about 6.0 and about 8.0.

52. The method of claim 51, wherein said pH is about 6.2±0.2.

53. The method of claim 44, wherein said reaction mixture contains a reducing agent in a concentration of about 1 to 15 $\mu$M.

54. The method of claim 44, wherein said fragments are separated from unincorporated methyl groups present in said reaction mixture after said isoaspartate residues in said fragments have been methylated.

55. The method of claim 54, wherein said fragments are separated by high-performance liquid chromatography (HPLC).

56. The method according to claim 44, wherein said labeled methyl groups comprise radioactively labeled S-adenosyl-L-methionine.

57. The method according to claim 56, wherein said step of determining the amount of isoaspartate residues comprises evaluating the incorporation of said radioactively labeled S-adenosyl-L-methionine into said fragments with an on-line radiometric detector.

58. The method of claim 56, wherein the radioactive label is tritium.

59. The method of claim 44, wherein said protein is broken into a plurality of polypeptide fragments by digesting said polypeptide with a proteolytic enzyme.

60. The method of claim 59, wherein said proteolytic enzyme is trypsin.

61. The method of claim 60, wherein said inhibiting step is accomplished by adding a trypsin inhibitor to said reaction mixture.

62. The method of claim 61, wherein said trypsin inhibitor is phenylmethylsulfonyl fluoride (PMSF).

* * * * *